United States Patent
Rauchfuss et al.

(10) Patent No.: US 8,324,409 B2
(45) Date of Patent: Dec. 4, 2012

(54) EFFICIENT METHOD FOR PREPARING 2,5-DIMETHYLFURAN

(75) Inventors: Thomas B. Rauchfuss, Urbana, IL (US); Todsapon Thananatthanachon, Lamphun (TH)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 13/092,816

(22) Filed: Apr. 22, 2011

(65) Prior Publication Data

US 2011/0263880 A1    Oct. 27, 2011

Related U.S. Application Data

(60) Provisional application No. 61/327,618, filed on Apr. 23, 2010.

(51) Int. Cl.
 *C07D 307/36* (2006.01)
 *C07D 307/44* (2006.01)
 *C07D 307/48* (2006.01)

(52) U.S. Cl. ............... 549/506; 549/483; 549/497

(58) Field of Classification Search .......... 549/483, 549/506

See application file for complete search history.

(56) References Cited

U.S. PATENT DOCUMENTS

| | | | |
|---|---|---|---|
| 2,098,592 | A | 11/1937 | Perkins et al. |
| 2,470,070 | A | 5/1949 | Heilbron et al. |
| 3,919,261 | A | 11/1975 | Merkle et al. |
| 4,013,684 | A | 3/1977 | Merkle et al. |
| 4,207,243 | A | 6/1980 | Linhart et al. |
| 4,243,593 | A | 1/1981 | Fremont et al. |
| 4,335,049 | A | 6/1982 | Hamada et al. |
| 4,533,743 | A | 8/1985 | Medeiros et al. |
| 4,590,283 | A | 5/1986 | Gaset et al. |
| 6,706,900 | B2 | 3/2004 | Grushin et al. |
| 7,064,222 | B2 | 6/2006 | Ahmed |
| 7,317,116 | B2 | 1/2008 | Sanborn |
| 7,393,963 | B2 | 7/2008 | Sanborn et al. |
| 7,572,925 | B2 | 8/2009 | Dumesic et al. |
| 7,579,489 | B2 | 8/2009 | Sanborn |
| 7,579,490 | B2 | 8/2009 | Sanborn et al. |
| 2008/0033187 | A1 | 2/2008 | Zhao et al. |
| 2008/0033188 | A1 | 2/2008 | Dumesic et al. |

FOREIGN PATENT DOCUMENTS

| | | |
|---|---|---|
| WO | 01/72732 A2 | 10/2001 |
| WO | 2006/063220 A2 | 6/2006 |
| WO | 2008/019219 A1 | 2/2008 |
| WO | 2009/030509 A2 | 3/2009 |
| WO | 2009/030511 A1 | 3/2009 |
| WO | 2009/030510 A4 | 8/2009 |
| WO | 2009/156439 A1 | 12/2009 |

OTHER PUBLICATIONS

Luijkx, Ether Formation in the Hydrogenolysis of Hydroxymethylfurfural over Palladium Catalysts in Alcoholic Solution, 2009, Heterocycles, vol. 77, No. 2, p. 1037-1044.*
Kumar et al., "Bioconversion of lignocellulosic biomass: biochemical and molecular perspectives", The Journal of Industrial Microbiology and Biotechnology, vol. 35, 2008, pp. 377-391.
Binder et al., "Simple Chemical Transformation of Lignocellulosic Biomass into Furans for Fuels and Chemicals", Journal of the American Chemical Society, vol. 131, No. 5, 2009, pp. 1979-1985.
Schiweck et al., "New Developments in the Use of Sucrose as an Industrial Bulk Chemical", Zuckerind, vol. 115, No. 7, 1990, pp. 555-565.
Metzger, Jurgen O., "Production of Liquid Hydrocarbons from Biomass", Angewandte Chemie International Edition, vol. 45, 2006, pp. 696-698.
Mehdi et al., "Integration of Homogeneous and Heterogeneous Catalytic Processes for a Multi-step Conversion of Biomass: From Sucrose to Levulinic Acid, γ-Valerolactone, 1,4-Pentanediol, 2-Methyl-tetrahydrofuran, and Alkanes", Topics in Catalysis, vol. 48, 2008, pp. 49-54.
Earle et al., "Ionic liquids. Green solvents for the future", Pure and Applied Chemistry, vol. 72, No. 7, 2000, pp. 1391-1398.
Sheldon, Roger, "Catalytic reactions in ionic liquids", Chemical Communications, 2001, pp. 2399-2407.
Kuster et al., "5-Hydroxymethylfurfural (HMF). A Review Focussing on its Manufacture", Starch/Stärke, vol. 42, No. 8, 1990, pp. 314-321.
Lichtenthaler, Frieder W., "Unsaturated 0- and N-Heterocycles from Carbohydrate Feedstocks", Accounts of Chemical Research, vol. 35, 2002, pp. 728-737.
Roman-Leshkov, et al., "Production of dimethylfuran for liquid fuels from biomass-derived carbohydrates", Nature, vol. 447, 2007, pp. 982-985.
Huber et al., "Synthesis of Transportation Fuels from Biomass: Chemistry, Catalysts, and Engineering", Chemical Reviews, 2006, 55 pages.
Schiweck et al., "New Developments in the Use of Sucrose as an Industrial Bulk Chemical", Carbohydrates as Organic Raw Materials, Chapter 3, Edited by: Frieder W. Lichtenthaler, 1990, pp. 57-94.

* cited by examiner

*Primary Examiner* — Golam M M Shameem
*Assistant Examiner* — Karen Cheng
(74) *Attorney, Agent, or Firm* — Morrison & Foerster LLP

(57) ABSTRACT

The present disclosure provides methods to make liquid fuels from renewable, carbon neutral precursors. Specifically, methods to prepare 2,5-dimethylfuran from a source of fructose or other carbohydrates using a one-pot synthesis are provided. In some embodiments, the disclosed methods avoid the isolation of intermediates, and employ "green" reagents like formic acid and acetic acid.

12 Claims, 17 Drawing Sheets

A)

B)

EFFICIENT METHOD FOR PREPARING 2,5-DIMETHYLFURAN

CROSS REFERENCE TO RELATED APPLICATIONS

This application claims the benefit under 35 USC 119(e) of prior U.S. Provisional Patent Application No. 61/327,618, filed Apr. 23, 2010, the disclosure of which is hereby incorporated by reference in its entirety.

TECHNICAL FIELD

The application is related to methods for preparing 2,5-dimethylfuran from a source of fructose or other carbohydrate.

BACKGROUND 2,5-Dimethylfuran (DMF) has great potential for use and application as a biofuel or liquid fuel. First, it has a nearly ideal boiling point (92° C.), which is about 14° C. higher than ethanol's boiling point (78° C.). Second, it has a high energy density (30 kJ/cm$^3$), and a high research octane number (RON=119), making it comparable to gasoline (Y. Román-Leshkov, C. J. Barrett, Z. Y. Liu, J. A. Dumesic, *Nature* 2007, 447, 982-985). Furthermore, DMF is immiscible with water and easier to blend with gasoline than ethanol, which is currently biofuel. 2,5-Dimethylfuran (DMF) is a heterocyclic compound with the following formula:

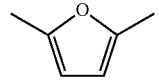

Several methods are known in the art to produce DMF. U.S. Pat. No. 2,098,592 discloses a process to synthesize DMF by pyrolyzing acetone at a temperature above 700° C. for less than a second, and then immediately cooling the reaction gases in a liquid medium. DMF can be isolated from the resulting liquid mixture. In another example, U.S. Pat. No. 2,470,070 discloses a process to synthesize DMF by heating hex-3-en-5-yn-2-ol to 100° C. in the presence of a mercuric catalyst to form DMF. Yet another example is the catalytic conversion of fructose to DMF (Y. Román-Leshkov, et al., *Nature* 2007, 447, 982-985); however, this process requires two separate reactions. First, fructose is dehydrated to 5-(hydroxymethyl)fufural (HMF), catalyzed by $H_2SO_4$. Then, HMF is converted to DMF using a CuRu/C catalyst, and $H_2$ at high temperature (220° C.) and high pressure (6.8 bar). In this process, the HMF intermediate from the first step has to be isolated and purified before processing to the second step.

There remains an unmet need for new methods to produce DMF in a one-pot process, using a "green" synthetic route that does not require the use and generation of hazardous substances, and the generation of unwanted waste. The methods disclosed herein address these unmet needs.

SUMMARY

Glucose readily isomerizes to fructose, from which a number of liquid fuels and their intermediates are contemplated, as shown below.

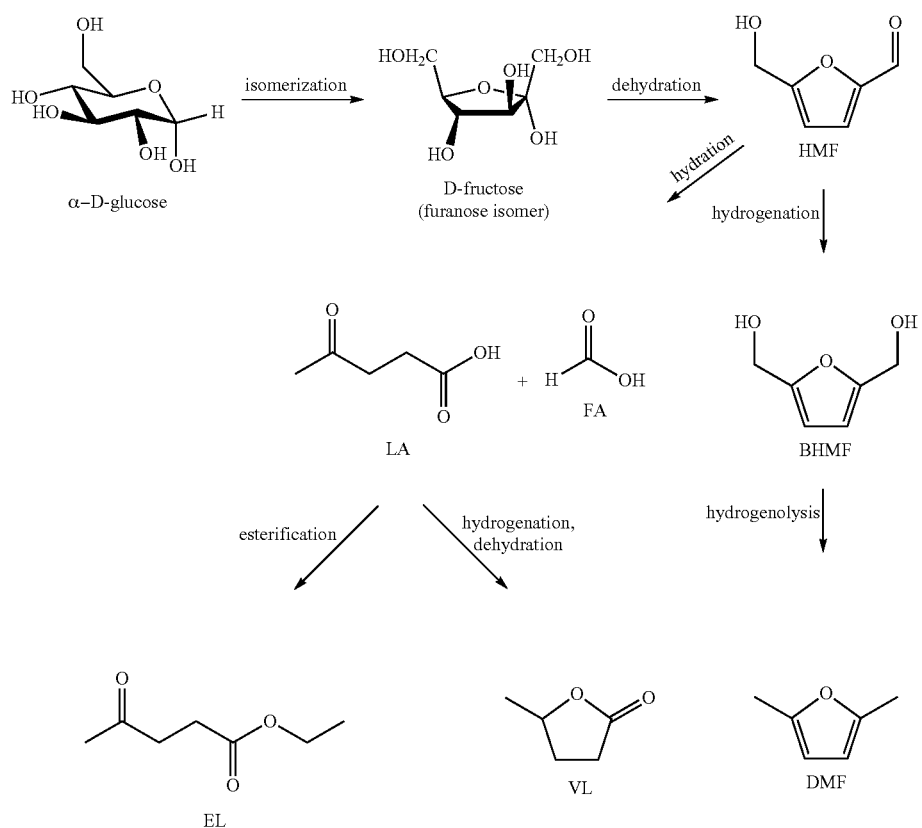

The present disclosure provides new methods to prepare 2,5-dimethylfuran (DMF) from a carbohydrate source. In one example, the multi-step process involves dehydration of fructose to form the intermediate HMF, which is then hydrogenated to form the bis alcohol, BHMF. Esterification of BHMF followed by hydrogenolysis of the ester provides the DMF product. The invention also discloses a method of preparing DMF from the key compound intermediate HMF or BHMF. Methods to produce products related to DMF, such as 2-methylfuran and 2-methyltetrahydrofuran, as well as compound intermediates, such as HMF and BHMF, are also disclosed. In a particular embodiment, formic acid is identified as a key reagent that can serve as an acid catalyst, a source of hydrogen and a deoxygenation agent in the multistep process of converting sugars to DMF. In one embodiment, the disclosed methods involve a one-pot, multi-step process.

In one aspect, the present disclosure provides a method for preparing 2,5-dimethylfuran, which includes the steps of: a) combining a source of carbohydrate with a carboxylic acid; b) heating the reaction mixture of step (a) to a temperature sufficient to form 5-(hydroxymethyl)furfural (HMF), an ester of HMF or a combination thereof; c) adding a first catalyst to the reaction mixture of step (b) and optionally an aprotic solvent; and d) heating the reaction mixture of step (c) to form 2,5-dimethylfuran.

In another aspect, the present disclosure provides a method for preparing 2,5-dimethylfuran, which includes the steps of: a) combining a source of carbohydrate with a carboxylic acid; b) heating the reaction mixture of step (a) to a temperature sufficient to form 5-(hydroxymethyl)furfural (HMF); c) adding $H_2$, a first catalyst, and optionally an aprotic solvent to the reaction mixture of step (b); d) reacting the mixture of step (c) to form 2,5-bis(hydroxymethyl)furan (BHMF); e) adding a second catalyst to the reaction mixture of step (d) to form an ester of BHMF; and f) hydrogenolysis of the ester of step (e) to form 2,5-dimethylfuran.

In another aspect, the present disclosure provides a method for preparing 2,5-dimethylfuran, which includes the steps of: a) combining 5-(hydroxymethyl)furfural (HMF) with $H_2$, a first catalyst, and an aprotic solvent; b) reacting the mixture of step (a) to form 2,5-bis(hydroxymethyl)furan (BHMF); c) adding a carboxylic acid, and a second catalyst to the reaction mixture of step (b) to form an ester of BHMF; and d) adding $H_2$ to the reaction mixture that includes the ester of BHMF of step (c) to form 2,5-dimethylfuran.

In yet another aspect, the present disclosure provides a method for preparing 2,5-dimethylfuran, which includes the steps of: a) combining 5-(hydroxymethyl)furfural (HMF) with formic acid, a first catalyst, wherein the first catalyst is a strong acid catalyst; a second catalyst; and an aprotic solvent; and b) heating the reaction mixture of step (a) to form 2,5-dimethylfuran.

In one aspect, the present disclosure provides a method for preparing DMF or a derivative thereof, which includes the steps of: a) combining a compound of formula I with a carboxylic acid and a strong acid catalyst, wherein formula I has the structure:

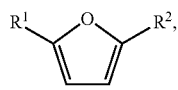

wherein $R^1$ and $R^2$ are each independently selected from the group consisting of hydrogen, $CH_2OH$, $CH_3$, and $CH(=O)$; b) heating the reaction mixture of step (a) to a temperature sufficient to form an ester of formula I; c) adding an aprotic solvent and a first catalyst to the reaction mixture of step (b); and d) heating the reaction mixture of step (c) under hydrogen to form a product selected from the group consisting of DMF, 2,5-dimethyltetrahydrofuran, 2-methylfuran, 2-methyltetrahydrofuran.

In another aspect, the present disclosure provides a method for preparing BHMF using formic acid, which includes the steps of: a) combining HMF with a first catalyst, an aprotic solvent; b) heating the reaction mixture; and c) adding to the reaction mixture of step (b) an amount of formic acid to form BHMF.

In yet another aspect, the present disclosure provides a method for preparing BHMF using formic acid, which includes the steps of: a) combining a source of carbohydrate with formic acid; b) reacting the mixture of step (a) to form HMF; c) adding a first catalyst and a base to the reaction mixture of step (b); and d) reacting the mixture of step (c) to form BHMF. The disclosure describes methods to make liquid fuels from renewable precursors. In some embodiments, the precursors are carbon-neutral and the methods do not generate undesirable waste.

In yet another aspect, the present disclosure provides a method for preparing HMF, which includes the steps of: a) combining a source of carbohydrate with a solid acid catalyst, and two or more aprotic solvents; and b) heating the mixture of step (a) to a temperature sufficient to form HMF.

In yet another aspect, the present disclosure provides a method for preparing a mixture of HMF and FMF, which includes the steps of: a) combining a source of carbohydrate with solid acid catalyst, and formic acid; and b) heating the mixture of step (a) to a temperature sufficient to form a mixture of HMF and FMF.

BRIEF DESCRIPTION OF THE DRAWINGS

NMR samples of the crude products were prepared by sampling out 1 mL of the reaction mixture. Unless otherwise indicated, the spectra were recorded without concentrating the solution or addition of deuterated solvent.

MODES OF CARRYING OUT THE INVENTION

Figure 1:
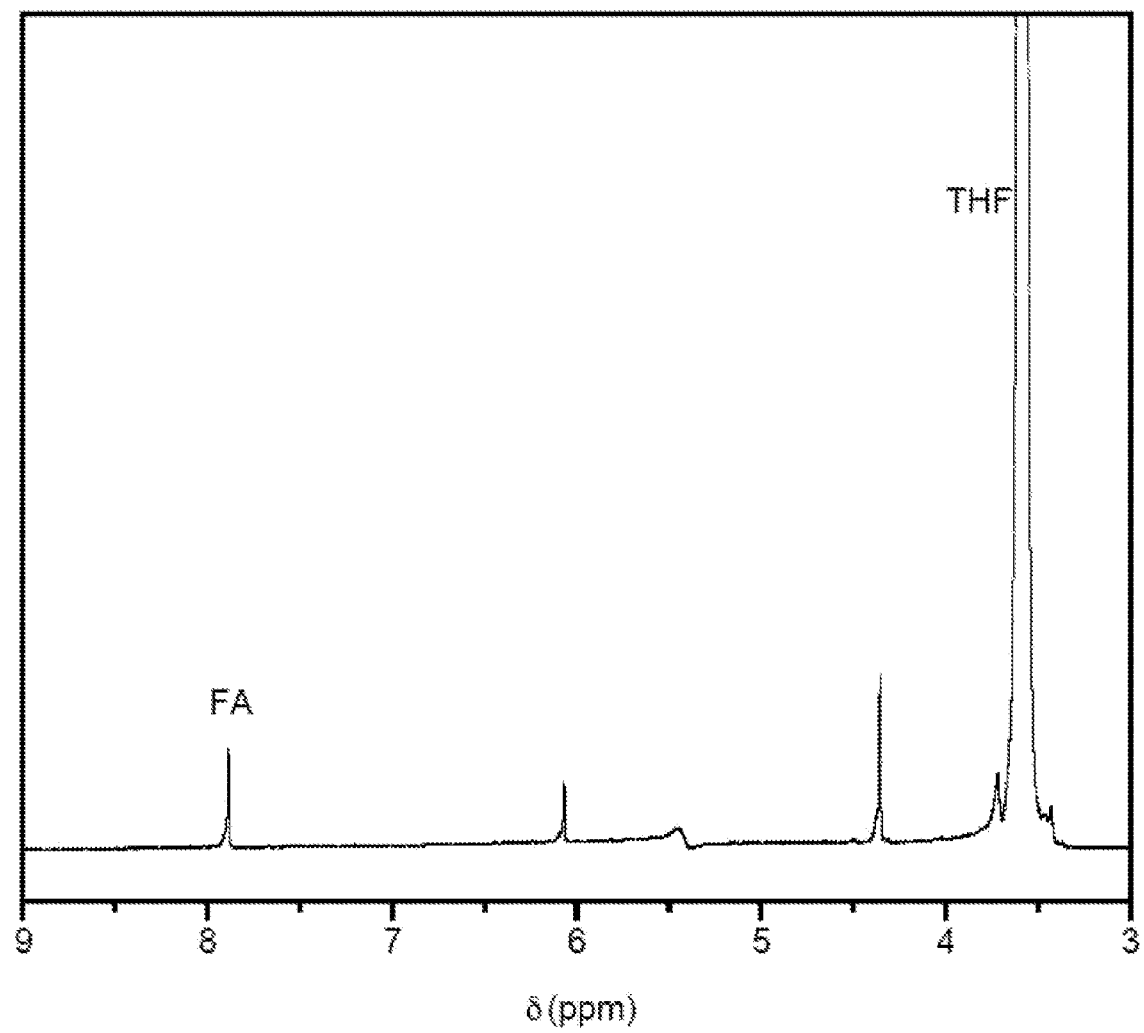
FIG. 1 is a $^1H$ NMR spectrum of a crude sample from the hydrogenation of HMF using FA and Pd/C catalyst.

Abbreviations.

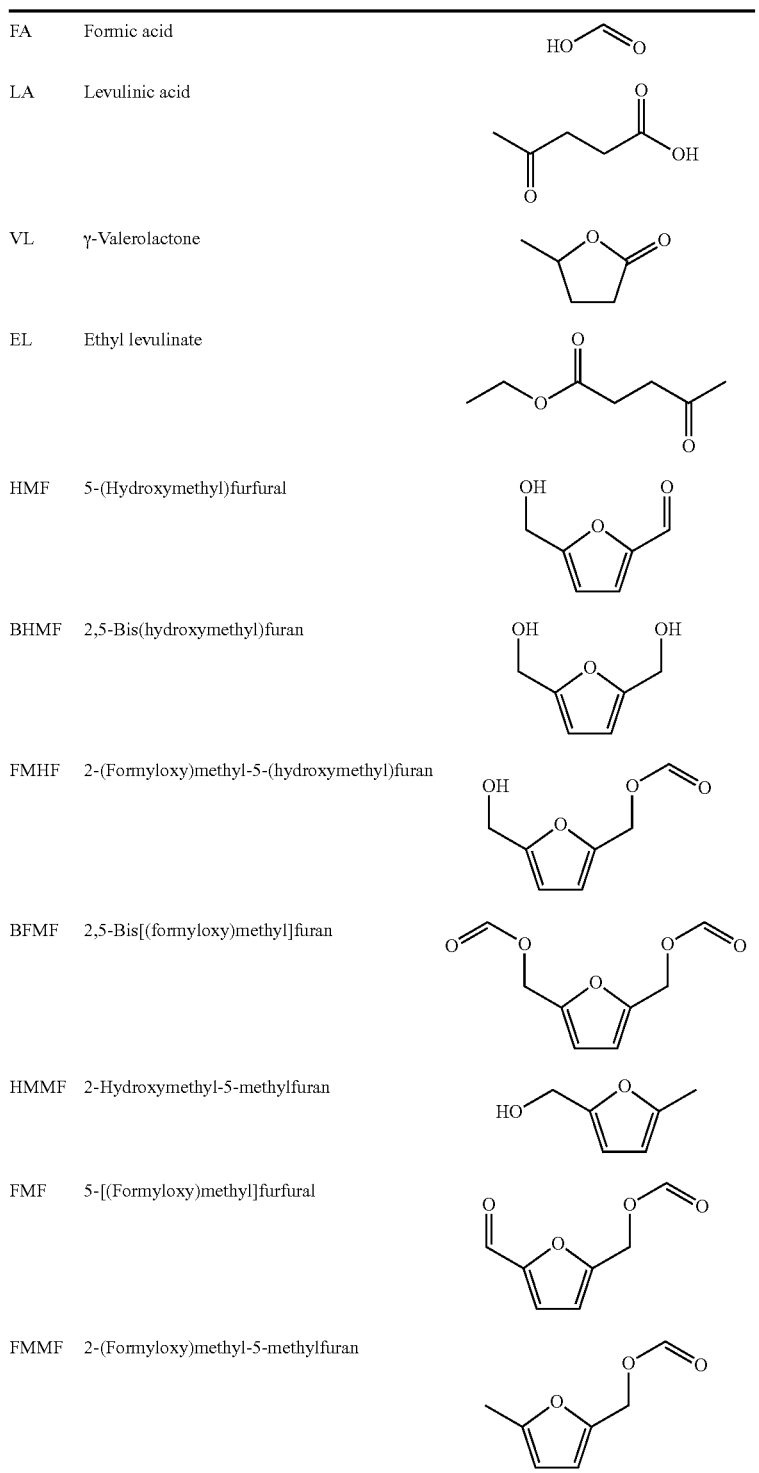

| | | |
|---|---|---|
| DMF | 2,5-Dimethylfuran | 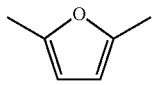 |
| AMF | 5-[(Acetoxy)methyl]furfural | 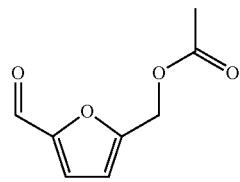 |
| BAMF | 2,5-Bis[(acetoxy)methyl]furan | 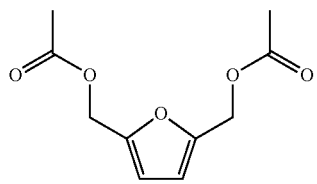 |
| HMTF | 2-Hydroxymethyl-5-(methyl)tetrahydrofuran | 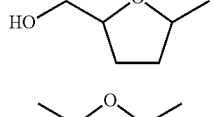 |
| DTF | 2,5-Dimethyltetrahydrofuran | 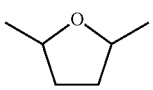 |

In one aspect, the present disclosure provides a method A for preparing 2,5-dimethylfuran, which includes the steps of: a) combining a source of carbohydrate with a carboxylic acid; b) heating the reaction mixture of step (a) to a temperature sufficient to form 5-(hydroxymethyl)furfural (HMF), an ester of HMF or a combination thereof; c) adding a first catalyst to the reaction mixture of step (b) and optionally an aprotic solvent; and d) heating the reaction mixture of step (c) to form 2,5-dimethylfuran. In one embodiment, steps (a)-(d) are carried out in one reaction vessel. In some embodiments of method A, the reaction intermediate of step (b) is not isolated or purified before continuing to step (c).

In some embodiments of method A, the first catalyst of step (c) is a metal catalyst, wherein the metal catalyst is any one or more metal catalyst selected from the group consisting of palladium, iridium, platinum, ruthenium, nickel, rhodium, scandium, titanium, vanadium, chromium, manganese, iron, cobalt, copper, zinc, yttrium, zirconium, niobium, molybdenum, technetium, silver, cadmium, lanthanum, hafnium, tantalum, tungsten, rhenium, osmium, gold, and mercury.

In some embodiments of method A, the aprotic solvent of step (c) is any one or more aprotic solvent selected from the group consisting of 1-methyl-2-pyrrolidinone (NMP), dimethylacetamide (DMA), dimethylformamide, dimethyl sulfoxide (DMSO), methyl ethyl ketone (MEK), methyl isobutylketone, acetonitrile (ACN), propionitrile, dichloromethane ($CH_2Cl_2$), ethyl acetate, acetone, tetrahydrofuran (THF), 1,4-dioxane, chloroform, butyl acetate, sulfolane, 1,2-dimethyoxyethane, toluene, benzene, hexanes, heptane, pentane, cycloheptane, cyclohexane, xylenes, and combinations thereof. In some embodiments of method A, the aprotic solvent of step (c) is any one or more aprotic solvent selected from the group consisting of THF, DMSO, DMF, NMP, and $CH_2Cl_2$ In some embodiments of method A, the aprotic solvent of step (c) is DMSO or THF.

In some embodiments of method A, step (c) further includes adding a second catalyst and an aprotic solvent to the reaction mixture of step (b) in addition to the first catalyst; wherein the second catalyst is a strong acid catalyst. In specific embodiments of method A, the strong acid catalyst is any one or more strong acid catalyst selected from the group consisting of sulfuric acid, hydrochloric acid, perchloric acid, hydrobromic acid, hydroiodic acid, p-toluenesulfonic acid, nitric acid, trifluoromethanesulfonic acid, methanesulfonic acid, and trifluoroacetic acid. In other embodiments of method A, the strong acid catalyst is a solid strong acid catalyst. In specific embodiments of method A, the carboxylic acid of step (a) is formic acid; the amount of formic acid to carbohydrate is less than or about 4 equivalents; and the amount of strong acid catalyst to carbohydrate is about or less than 3%.

In some embodiments of method A, the method further includes adding DMSO to the reaction mixture of step (a).

In some embodiments of method A, the amount of carboxylic acid of step (a) is about 10 mol % of the carbohydrate. In specific embodiments of method A, the carboxylic acid of step (a) is formic acid. In alternative embodiments of method A, the carboxylic acid of step (a) is acetic acid.

In some embodiments of method A, the method further includes adding hydrogen gas to the reaction mixture of step (c).

In some embodiments of method A, the method further includes cooling the reaction mixture of step (b) to room temperature before step (c).

In some embodiments of method A, the source of carbohydrate is a biomass optionally selected from a microbial biomass, animal biomass, or plant-based biomass. In specific embodiments of method A, the carbohydrate is a monosaccharide.

In another aspect, the present disclosure provides a method B for preparing 2,5-dimethylfuran, which includes the steps of: a) combining a source of carbohydrate with a carboxylic acid; b) heating the reaction mixture of step (a) to a temperature sufficient to form 5-(hydroxymethyl)furfural (HMF); c) adding $H_2$, a first catalyst, and optionally an aprotic solvent to the reaction mixture of step (b); d) reacting the mixture of step (c) to form 2,5-bis(hydroxymethyl)furan (BHMF); e) adding a second catalyst to the reaction mixture of step (d) to form an ester of BHMF; and f) hydrogenolysis of the ester of step (e) to form 2,5-dimethylfuran. In one embodiment, steps (a)-(d) are carried out in one reaction vessel.

In some embodiments of method B, the carboxylic acid is any one or more carboxylic acid selected from the group consisting of formic acid, acetic acid, benzoic acid, trifluoroacetic acid, propionic acid, and trichloroacetic acid.

In some embodiments of method B, the first catalyst is a metal catalyst, wherein the metal catalyst is any one or more metal catalyst selected from the group consisting of palladium, iridium, platinum, ruthenium, nickel, rhodium, scandium, titanium, vanadium, chromium, manganese, iron, cobalt, copper, zinc, yttrium, zirconium, niobium, molybdenum, technetium, silver, cadmium, lanthanum, hafnium, tantalum, tungsten, rhenium, osmium, gold, and mercury. In some embodiments of method B, the second catalyst of step (e) is a strong acid catalyst.

In some embodiments of method B, the hydrogenolysis step (e) includes adding $H_2$ to the reaction mixture that includes the ester of step (d).

In some embodiments of method B, the hydrogenolysis step (e) further includes adding a metal catalyst, wherein the metal catalyst is any one or more metal catalyst selected from the group consisting of palladium, iridium, platinum, ruthenium, nickel, rhodium, scandium, titanium, vanadium, chromium, manganese, iron, cobalt, copper, zinc, yttrium, zirconium, niobium, molybdenum, technetium, silver, cadmium, lanthanum, hafnium, tantalum, tungsten, rhenium, osmium, gold, and mercury, to the reaction mixture that includes the ester of step (d). In specific embodiments of method B, the $H_2$ applied to the reaction mixture is less than about 200 psi.

In another aspect, the present disclosure provides a method C for preparing 2,5-dimethylfuran, which includes the steps of: a) combining 5-(hydroxymethyl)furfural (HMF) with $H_2$, a first catalyst, and an aprotic solvent; b) reacting the mixture of step (a) to form 2,5-bis(hydroxymethyl)furan (BHMF); c) adding a carboxylic acid, and a second catalyst to the reaction mixture of step (b) to form an ester of BHMF; and d) adding $H_2$ to the reaction mixture that includes the ester of BHMF of step (c) to form 2,5-dimethylfuran.

In some embodiments of method C, the first catalyst is a metal catalyst, wherein the metal catalyst is any one or more metal catalyst selected from the group consisting of palladium, iridium, platinum, ruthenium, nickel, rhodium, scandium, titanium, vanadium, chromium, manganese, iron, cobalt, copper, zinc, yttrium, zirconium, niobium, molybdenum, technetium, silver, cadmium, lanthanum, hafnium, tantalum, tungsten, rhenium, osmium, gold, and mercury. In some embodiments of method C, the second catalyst is a strong acid catalyst.

In some embodiments of method C, the carboxylic acid is any one or more carboxylic acid selected from the group consisting of formic acid, acetic acid, benzoic acid, trifluoroacetic acid, propionic acid, and trichloroacetic acid.

In some embodiments of method C, the $H_2$ applied to the reaction mixture in step (d) is less than about 200 psi.

In yet another aspect, the present disclosure provides a method D for preparing 2,5-dimethylfuran, which includes the steps of: a) combining 5-(hydroxymethyl)furfural (HMF) with formic acid, a first catalyst, wherein the first catalyst is a strong acid catalyst; a second catalyst; and an aprotic solvent; and b) heating the reaction mixture of step (a) to form 2,5-dimethylfuran.

In some embodiments of method D, the second catalyst is a metal catalyst, wherein the metal catalyst is any one or more metal catalyst selected from the group consisting of palladium, iridium, platinum, ruthenium, nickel, rhodium, scandium, titanium, vanadium, chromium, manganese, iron, cobalt, copper, zinc, yttrium, zirconium, niobium, molybdenum, technetium, silver, cadmium, lanthanum, hafnium, tantalum, tungsten, rhenium, osmium, gold, and mercury.

In some embodiments of method D, the strong acid catalyst of step (a) is any one or more strong acid catalyst selected from the group consisting of sulfuric acid, hydrochloric acid, perchloric acid, hydrobromic acid, hydroiodic acid, p-toluenesulfonic acid, nitric acid, trifluoromethanesulfonic acid, methanesulfonic acid, and trifluoroacetic acid. In some embodiments of method D, the strong acid catalyst is a solid strong acid catalyst.

In some embodiments of method D, the amount of formic acid to HMF in step (a) is less than 6 equivalents and the amount of strong acid catalyst to HMF less than 6 mol %.

In one aspect, the present disclosure provides a method E for preparing DMF or a derivative thereof, which includes the steps of: a) combining a compound of formula I with a carboxylic acid and a strong acid catalyst, wherein formula I has the structure:

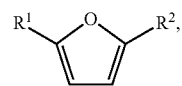

wherein $R^1$ and $R^2$ are each independently selected from the group consisting of hydrogen, $CH_2OH$, $CH_3$, and $CH(=O)$; b) heating the reaction mixture of step (a) to a temperature sufficient to form an ester of formula I; c) adding an aprotic solvent and a first catalyst to the reaction mixture of step (b); and d) heating the reaction mixture of step (c) under hydrogen to form a product selected from the group consisting of DMF, 2,5-dimethyltetrahydrofuran, 2-methylfuran, 2-methyltetrahydrofuran.

In some embodiments of method E, the carboxylic acid is any one or more carboxylic acid selected from the group consisting of formic acid, acetic acid, benzoic acid, trifluoroacetic acid, propionic acid, and trichloroacetic acid. In some embodiments of method E, the first catalyst of step (c) is a metal catalyst, wherein the metal catalyst is any one or more metal catalyst selected from the group consisting of palladium, iridium, platinum, ruthenium, nickel, rhodium, scandium, titanium, vanadium, chromium, manganese, iron, cobalt, copper, zinc, yttrium, zirconium, niobium, molybdenum, technetium, silver, cadmium, lanthanum, hafnium, tantalum, tungsten, rhenium, osmium, gold, and mercury.

In some embodiments of method E, formula I is selected from the group consisting of

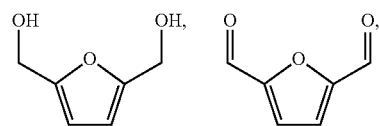

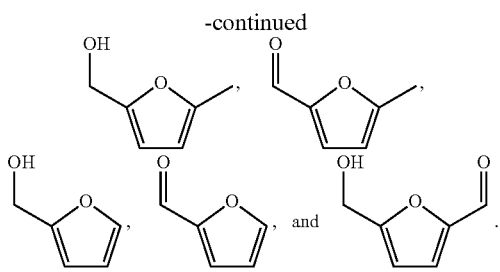

In another aspect, the present disclosure provides a method F for preparing BHMF using formic acid, which includes the steps of: a) combining HMF with a first catalyst, an aprotic solvent; b) heating the reaction mixture; and c) adding to the reaction mixture of step (b) an amount of formic acid to form BHMF. In some embodiments of method F, the first catalyst is a metal catalyst, wherein the metal catalyst is any one or more metal catalyst selected from the group consisting of palladium, iridium, platinum, ruthenium, nickel, rhodium, scandium, titanium, vanadium, chromium, manganese, iron, cobalt, copper, zinc, yttrium, zirconium, niobium, molybdenum, technetium, silver, cadmium, lanthanum, hafnium, tantalum, tungsten, rhenium, osmium, gold, and mercury.

In yet another aspect, the present disclosure provides a method G for preparing BHMF using formic acid, which includes the steps of: a) combining a source of carbohydrate with formic acid; b) reacting the mixture of step (a) to form HMF; c) adding a first catalyst and a base to the reaction mixture of step (b); and d) reacting the mixture of step (c) to form BHMF. In one embodiment of method G, the first catalyst of step (c) is a metal catalyst, wherein the metal catalyst is any one or more metal catalyst selected from the group consisting of palladium, iridium, platinum, ruthenium, nickel, rhodium, scandium, titanium, vanadium, chromium, manganese, iron, cobalt, copper, zinc, yttrium, zirconium, niobium, molybdenum, technetium, silver, cadmium, lanthanum, hafnium, tantalum, tungsten, rhenium, osmium, gold, and mercury.

In yet another aspect, the present disclosure provides a method H for preparing HMF, which includes the steps of: a) combining a source of carbohydrate with a solid acid catalyst, and two or more aprotic solvents; and b) heating the reaction mixture of step (a) to a temperature sufficient to form HMF. In a specific embodiment of method H, the solid acid catalyst is Amberlyst 15. Functional equivalents to Amberlyst 15 may be substituted herein.

In some embodiments of method H, the two or more aprotic solvents of step (a) include a first aprotic solvent and a second aprotic solvent, wherein the first aprotic solvent is DMSO, and the second aprotic solvent is THF or an organic solvent miscible with the first aprotic solvent. In some embodiments of method H, the two or more aprotic solvents of step (a) include a first aprotic solvent and a second aprotic solvent, wherein the first aprotic solvent is DMSO, and the second aprotic solvent is selected from the group consisting of THF, 1-methyl-2-pyrrolidinone (NMP), dimethylacetamide (DMA), dimethylformamide, methyl ethyl ketone (MEK), methyl isobutylketone, acetonitrile (ACN), propionitrile, dichloromethane ($CH_2Cl_2$), ethyl acetate, acetone, 1,4-dioxane, chloroform, butyl acetate, sulfolane, 1,2-dimethyoxyethane, toluene, benzene, and combinations thereof. In some embodiments of method H, the two or more aprotic solvents of step (a) are two aprotic solvents, wherein the two aprotic solvents are DMSO and THF.

In yet another aspect, the present disclosure provides a method I for preparing a mixture of HMF and FMF, which includes the steps of: a) combining a source of carbohydrate with solid acid catalyst, and formic acid; and b) heating the reaction mixture of step (a) to a temperature sufficient to form a mixture of HMF and FMF. In a specific embodiment of method I, the solid acid catalyst is Amberlyst 15. Functional equivalents to Amberlyst 15 may be substituted herein. In some embodiments of method I, the method further includes adding one or more molecular sieves to the reaction mixture of step (a).

In some of the foregoing embodiments, the disclosed processes are performed as a "one-pot" reaction. In one embodiment, for instance, the FMF or HMF intermediate formed in the first step of the synthesis is not isolated from the reaction mixture or purified. Instead, the entire reaction mixture is used in the next step of the process, in which FMF is converted to DMF. The one-pot reaction eliminates the effort and expense of the HMF, FMF or any other reaction intermediate (such as HMMF, FMMF, BHMF, and FMHF) isolation step. However, it will be understood to persons skilled in the art that HMF, FMF or any other reaction intermediate (such as HMMF, FMMF, BHMF, and FMHF) may be isolated from the reaction mixture before continuing with the next reaction step. In some of the foregoing embodiments, the methods are carried out in a single reaction vessel. In some of the foregoing embodiments, the reaction intermediates are used in the next step of the process without isolation or purification. In some of the foregoing embodiments, the reaction steps herein are carried out in one reaction vessel. In some of the foregoing embodiments, the reaction steps herein are carried out using a continuous flow reactor. In alternative embodiments, certain reaction intermediates (such as HMF, FMF, HMMF, FMMF, BHMF, or FMHF) are isolated prior to the next reaction.

In one aspect, the present disclosure provides a method for converting a monosaccharide to either DMF or a compound intermediate, including the use of formic acid as a reagent.

In some embodiments, the method includes the steps of combining HMF with formic acid and a metal catalyst to form a reaction mixture; and heating the reaction mixture to form BHMF.

In some embodiments, the method includes the steps of combining BHMF with formic acid and a strong acid catalyst to form a reaction mixture; and heating the reaction mixture to form BFMF.

In some embodiments, the method includes the steps of combining BHMF with formic acid and a strong acid catalyst to form a reaction mixture; and heating the reaction mixture to form FMHF.

In some embodiments, the method includes the steps of combining HMF, formic acid, a strong acid catalyst, an aprotic solvent and a metal catalyst to form a reaction mixture; and heating the reaction mixture to form DMF.

In some embodiments, the method includes the steps of a) combining a monosaccharide, and formic acid to form a reaction mixture; b) heating the reaction mixture of step (a) until the monosaccharide is substantially converted; c) adding an aprotic solvent, a strong acid catalyst, and a metal catalyst to the reaction mixture of step (b); and d) heating the reaction mixture of step (c) to form DMF.

In some embodiments, the step of heating the reaction mixture until the reaction is substantially complete is followed by the step of cooling the reaction mixture prior to the next step.

In a specific embodiment, the present disclosure provides a method to synthesize 2,5-dimethylfuran, which includes the steps of: a) combining a source of carbohydrate with formic acid; b) heating the reaction mixture of step (a) to a temperature sufficient to form 5-[(formyloxy)methyl]furfural; (c) adding an aprotic solvent and a palladium catalyst to the reaction mixture of step (b); and (d) heating the reaction mixture of step (c) to form 2,5-dimethylfuran. In one embodiment, the temperature in step (b) is sufficient to form one or more of 5-(hydroxymethyl)furfural and 5-[(formyloxy)methyl]furfural intermediates. In another embodiment, the preferred temperature in step (b) is about 120° C. to about 150° C. In one embodiment, the temperature in step (b) is about 150° C. In some embodiments, the reaction mixture in step (b) is heated for a time period of about one to about six hours. In some embodiments, the reaction mixture in step (b) is heated for about six hours. In some embodiments, the reaction mixture in step (d) is heated to reflux. In another embodiment, the reaction mixture in step (d) is heated to a temperature of about 65° C. to about 70° C. In another embodiment, the method further includes isolating 2,5-dimethylfuran. In one embodiment, the method further includes cooling the reaction mixture of step (d) to room temperature, and isolating 2,5-dimethylfuran. In another embodiment, the method further includes distilling the reaction mixture of step (d) to isolate 2,5-dimethylfuran. In another embodiment, the method includes the steps of: a) combining a source of carbohydrate with formic acid; b) heating the reaction mixture obtained in step (a) at a temperature of about 90° C. to about 150° C.; c) adding an aprotic solvent and a palladium catalyst to the reaction mixture of step (b); and d) heating the reaction mixture of step (c) to form 2,5-dimethylfuran. In some embodiments, the method further includes adding an acid catalyst to the reaction mixture of step (c).

Provided in this application are methods to prepare 2,5-dimethylfuran (DMF) in a single pot from a source of carbohydrate. As used herein, a "source of carbohydrate" includes, for instance, fructose, or hexoses, or any biomass that contains carbohydrates that will produce DMF. As used herein, a "source of fructose" includes, for instance, fructose itself, purified or crude, or any biomass that contains fructose or precursors to fructose, such as corn syrup, sucrose and polyfructanes. As used herein, "biomass" includes, for instance, a herbaceous or woody energy crop, an agricultural feed crop, a crop waste or crop residue, a wood waste or residue, an aquatic plant material, or municipal waste. In some embodiments, the carbohydrate is a monosaccharide. In some embodiments, the carbohydrate is fructose. In some embodiments the carbohydrate is a ketohexose. In some embodiments, the carbohydrate is a monosaccharide. In a specific embodiment, the carbohydrate is fructose.

In a one aspect, 2,5-dimethylfuran is prepared in one reaction vessel, without isolation of intermediates. In some embodiments, the method is a one-pot process with milder reaction conditions than traditional methods and utilizes a green hydrogen source and solvent, thereby avoiding the use and generation of unwanted hazardous substances. In some embodiments, the present disclosure is advantageous over what is currently known in the art because the method described herein achieves several conversions in "one-pot" such that the reaction vessel does not need to be changed. The one-pot reaction eliminates the effort and expense of isolating reaction intermediates prior to continuing to the next step in the reaction.

In some embodiments, formic acid, serves multiple roles: acid catalyst, hydrogen source, and esterification agent. Since the catalyst for hydrogenation and hydrogenolysis is heterogenous, product isolation is also simplified. Furthermore, the solvent, THF, is biomass-derived and could be recycled. One side product, levulinic acid, is also a promising fuel or fuel processor. The other side product, formic acid, accelerates the conversion of fructose to DMF.

In some of the foregoing embodiments, the method includes using a carboxylic acid in the reaction mixture. In some embodiments the carboxylic acid is used in the dehydration step, such as the dehydration of fructose to HMF. In certain embodiments, the carboxylic is used to form an ester with an alcohol of a reaction intermediate, such as HMF, BHMF, FMHF, HMMF, and HMTF. The alcohol and the carboxylic acid react to form and ester through a dehydration reaction. For instance, HMF reacts with acetic acid to form AMF; and HMF reacts with formic acid to form FMF. Examples of carboxylic acid include formic acid, acetic acid, oxalic acid, benzoic acid, trifluoroacetic acid, propionic acid, and trichloroacetic acid. In certain embodiments, the carboxylic acid is selected from the group consisting of formic acid and acetic acid.

In some embodiments, a catalyst is added to the reaction mixture that includes a source of carbohydrate and an acid. Catalysts include Bronsted and Lewis acids, transition metal salts and complexes and ion exchange resins. In some of the foregoing embodiments, a strong acid catalyst is used in a reaction step. Examples of strong acids include sulfuric acid ($H_2SO_4$), p-toluenesulfonic acid, hydrochloric acid (HCl), perchloric acid ($HClO_4$), hydrobromic acid (HBr) and hydroiodic acid (HI), p-toluenesulfonic acid, nitric acid, trifluoromethanesulfonic acid, methanesulfonic acid, and trifluoroacetic acid. In some of the foregoing embodiments, the strong acid catalyst is sulfuric acid.

Alternatively, in some of the foregoing embodiments a strong acid catalyst may be used in a solid form. A solid acid catalyst may include a solid material which has been functionalized to impart acid groups that are catalytically active. Solid acid catalysts may have a broad range of composition, porosity, density, type of acid groups and distribution of acid groups. Solid acid catalysts may be recovered and reused, optionally with a treatment to regenerate any activity that may have been lost in use. Examples of solid acid catalysts that may be used in the disclosed process include, but are not limited to Amberlyst 35, Amberlyst 36, Amberlyst 15, Amberlyst 131 (Rohm and Haas, Woodridge, Ill.), bio-Rad AG-50W resins, Lewatit S2328, Lewatit K2431, Lewatit S2568, Lewatit K2629 (Sybron Corp, Birmingham, N.J.), Dianion SK104, Dianion PK228, Dianion RCP160, RCP21 H, Relite RAD/F (Mitsubishi Chemical, White Plains, N.Y.), and Dowex-type ion-exchange resins, such as 50WX4 (Dow Chemical). In some of the foregoing embodiments, the strong acid catalyst is solid catalytic support that may include a strong acid resin. In some of the foregoing embodiments, the strong acid catalyst is Dowex.

In some of the foregoing embodiments, the carbohydrate is combined with formic acid. Formic acid is currently not used in the art as a reagent in the production of biofuels. Contrary to what is known in the art, FA is used in some of the foregoing embodiments as an acid catalyst, a source of hydrogen ($H_2$), and a deoxygenation agent in the conversion of fructose to DMF. FA is currently produced industrially by the hydration of carbon monoxide as well as the hydrogenation of carbon dioxide, both of which are relatively carbon-neutral.

In some of the foregoing embodiments, upon combining fructose and FA, the reaction mixture is heated to a temperature that forms one or more of the following intermediates: 5-[(formyloxy)methyl]furfural (HMF) and 5-[(formyloxy) methyl]furfural (FMF). If the reaction mixture is not already at the desired temperature, it may be heated until the desired temperature is attained. The time of reaction will vary with reaction conditions and yields, but is generally about one to six hours. Agitation of the reaction mixture may also be used in any of the foregoing embodiments. In some of the foregoing embodiments, the temperature range is about 90° C. to 150° C. In some of the foregoing embodiments, the temperature range is about 100° C. to 150° C. In some of the foregoing embodiments, the temperature range is about 40° C. to 100° C. In some of the foregoing embodiments, the temperature range is about 60° C. to 80° C.

In some of the foregoing embodiments, the multi-step reactions of the disclosed method are carried out in the same reaction vessel. In some of the foregoing embodiments, the methods are carried out without purification or isolation of the reaction intermediates.

In some of the foregoing embodiments, the method includes the formation of a formate ester intermediate which further forms DMF upon addition of an aprotic solvent slurry with a metal catalyst.

The term "aprotic solvent" includes, for instance, a solvent that cannot donate a hydrogen. Aprotic solvents can have a more polar character or a more non polar character. Within a category, solvents can be compared to each other and one described as more polar or more non-polar than the other. The polarity of a solvent can be described by the solvent's dielectric constant, dipole moment and its ability to hydrogen bond. In some of the foregoing embodiments, the aprotic solvent is polar. In alternative embodiments, the aprotic solvent is non-polar. Examples of aprotic solvents include but is not limited to 1-methyl-2-pyrrolidinone (NMP), dimethylacetamide (DMA), dimethylformamide, dimethyl sulfoxide (DMSO), methyl ethyl ketone (MEK), methyl isobutylketone, acetonitrile (ACN), propionitrile, dichloromethane ($CH_2Cl_2$), ethyl acetate, acetone, tetrahydrofuran (THF), 1,4-dioxane, chloroform, butyl acetate, sulfolane, 1,2-dimethyoxyethane, and combinations thereof. In some of the foregoing embodiments, the aprotic solvent is a hydrocarbon solvent. Hydrocarbon solvents include straight-chain, branched, cyclic, and aromatic solvents containing hydrogen and carbon atoms, and mixtures thereof. Hydrocarbon solvents can be saturated or unsaturated. Non-limiting examples of hydrocarbon solvents include toluene, benzene, hexanes, heptane, pentane, cycloheptane, cyclohexane, xylenes, and mixtures thereof.

A suitable solvent is one where the starting material is fairly soluble, where the solvent does not interfere with the reaction, and is stable at the reaction conditions. Other considerations include the boiling point of the solvent. Other characteristics of a suitable solvent include the promotion of the reaction rate, the formation of the reaction product, or the reduction of undesired products. In some of the foregoing embodiments, the aprotic solvent is THF. In some of the foregoing embodiments, the aprotic solvent is DMSO. In some of the foregoing embodiments, the method excludes protic solvents. In some of the foregoing embodiments, the method excludes alcohol as a solvent. In some of the foregoing embodiments, protic solvents, such as alcohols, that would react with formic or acetic acid and prevent the desired esterification of HMF are excluded as a solvent.

In some of the foregoing embodiments, a metal catalyst is used in a reaction step. For instance, in some of the foregoing embodiments a metal catalyst is used in the hydrogenation reaction of HMF to BHMF; or in the hydrogenolysis of esterified intermediates such as FMHF, FMMF, FMF, BAMF, BFMF, and AMF. In some of the foregoing embodiments the metal catalyst includes a metal complex. In some of the foregoing embodiments, the metal catalyst is tethered or supported on a solid support, such as palladium on carbon. In some of the foregoing embodiments, the metal catalyst is a precious metal. In some of the foregoing embodiments the metal catalyst is any one or more metal catalyst selected from the group consisting of palladium, iridium, platinum, ruthenium, nickel, rhodium, scandium, titanium, vanadium, chromium, manganese, iron, cobalt, copper, zinc, yttrium, zirconium, niobium, molybdenum, technetium, silver, cadmium, lanthanum, hafnium, tantalum, tungsten, rhenium, osmium, gold, and mercury. In some of the foregoing embodiments, the metal catalyst is selected from palladium, iridium, platinum, ruthenium, nickel, rhodium, chromium, manganese, iron, cobalt, copper, zinc, zirconium, silver, cadmium, osmium, and gold, or a combination thereof. In some of the foregoing embodiments, the metal catalyst is selected from palladium, nickel, iron, copper, zinc, and silver or a combination thereof. In more specific embodiments, the metal catalyst is selected from palladium, iridium, platinum, and ruthenium, or a combination thereof. In some of the foregoing embodiments, the metal catalyst is a palladium catalyst.

The term "palladium catalyst" includes, for instance, a catalyst made up of palladium (Pd) metal. Examples include but is not limited to $Pd_3(dba)_3$, $PdCl_2$, $Pd(OAc)_2$, $PdCl_2(dppf).CH_2Cl_2$, $Pd(PPb_3)_4$, and related catalysts which are complexes of phosphine ligands, and other suitable ligands including those containing P and/or N atoms for coordinating to the palladium atoms, and other simple palladium salts either in the presence or absence of ligands. Palladium catalysts include palladium and palladium complexes supported or tethered on solid supports, such as palladium on carbon, as well as palladium black, palladium clusters, or palladium clusters containing other metals. In some of the foregoing embodiments, the palladium catalyst is palladium on carbon (Pd/C).

In alternative embodiments, the metal catalyst is an iridium-based catalyst. Non-limiting examples of iridium-based catalysts include Cp*Ir(TsDPEN); Cp*Ir(NHCPh$_2$C$_6$H$_4$); and CP*IrH(TsDACH-H). In some instances, the activity of the metal catalyst is reduced in the presence of an acid. For instance, a 10% concentration of formic acid results in a substantial decrease of Ir catalytic activity. In some of the foregoing embodiments, the acid of the reaction mixture is neutralized by a base prior to the addition of the metal catalyst. For instance, in an example wherein an iridium based catalyst is incompatible with an acid, a base is added to the reaction mixture in an amount to neutralize formic acid prior to the addition of the iridium catalyst to the reaction mixture. Thus, the catalytic activity of the metal catalyst is significantly preserved in the neutralized reaction mixture compared to the non-neutralized reaction mixture. Refer to Example 21.

Examples of bases include inorganic bases, such as hydroxides of alkali metals and alkaline earth metals, and organic bases. Other examples of inorganic bases include potassium hydroxide, barium hydroxide, cesium hydroxide, sodium hydroxide, strontium hydroxide, calcium hydroxide, lithium hydroxide, rubidium hydroxide, magnesium hydroxide. Examples of organic bases include triethylamine, trimethylamine, pyridine, and methyl amine. Ammonia is also a base. In some embodiments, the base is triethylamine or sodium hydroxide. The amount of base used may be determined by the amount of acid needed to be neutralized. The type of base used may be determined the desired strength of the base and its ability to neutralize the reaction without producing undesirable side reactions or side products.

Insoluble catalysts, if used in any of the steps of the invention, may be removed from the reaction mixture before proceeding to the next step or at the end of a multi-step reaction process. The removal can be accomplished by methods known to a person having ordinary skill in the art, such as filtration, centrifugation or decantation, for instance. The reaction mixture can be cooled for ease of handling for the separation step. In some of the foregoing embodiments, the insoluble catalyst, or any insoluble material, may be washed with a solvent to extract desired product of the reaction.

In some of the embodiments, the reaction mixture contains an amount of catalyst. In some of the embodiments, the amount of catalyst in the reaction mixture is less than 15%. In some of the embodiments, the amount of catalyst in the reaction mixture is less than 10%. In some of the embodiments, the amount of catalyst in the reaction mixture is less than 5%. In some of the embodiments, the amount of catalyst in the reaction mixture is less than 2%. In some of the embodiments, the amount of catalyst in the reaction mixture is less than 1%. In some of the embodiments, the amount of catalyst in the reaction mixture is between 0.05% to 5%. In some of the embodiments, the amount of catalyst in the reaction mixture is between 1% to 3%. In some of the embodiments, the amount of catalyst in the reaction mixture is between 0.05% to 1.5%. In some of the embodiments, the amount of catalyst in the reaction mixture is between 0.5% to 1.5%.

In some of the foregoing embodiments, formic acid is used as a hydrogen source. In alternative embodiments, a source of hydrogen atoms is hydrogen gas. Hydrogen gas may be applied to reactions including the hydrogenation of HMF to BHMF; and the hydrogenolysis of an ester of BHMF to DMF. The hydrogen gas pressure applied to the reaction mixture and the amount of time the reaction mixture is exposed to hydrogen gas both have a role in the degree of hydrogenation of the compound. For instance, hydrogenolysis of BAMF at 150 psi at 90° C. for two hours gave the DMF product in 86% yield. However, applying 500 psi of hydrogen gas for 12 hours resulted in the formation of the saturated DTF compound. Refer to Example 17.

In some of the foregoing embodiments, $H_2$ is applied to the reaction mixture under pressure. In some of the foregoing embodiments, the pressure of $H_2$ is less than 1500 psi. In some of the foregoing embodiments, the pressure of $H_2$ is less than 1000 psi. In some of the foregoing embodiments, the pressure of $H_2$ is less than 500 psi. In some of the foregoing embodiments, the pressure of $H_2$ is less than 300 psi. In some of the foregoing embodiments, the pressure of $H_2$ is less than 250 psi. In some of the foregoing embodiments, the pressure of $H_2$ is less than 200 psi. In some of the foregoing embodiments, the pressure of $H_2$ is less than 150 psi. In some of the foregoing embodiments, the pressure of $H_2$ is between 50-250 psi. In some of the foregoing embodiments, the pressure of $H_2$ is between 15-175 psi. In some of the foregoing embodiments, the $H_2$ gas is bubbled through the reaction mixture. In some embodiments, the pressure of $H_2$ is less than 50 psi.

In some of the foregoing embodiments, one or more molecular sieves may be added to the reaction mixture. Without wishing to be bound by theory, it is believed that the addition of molecular sieves suppresses formation of levulinic acid in the dehydration step of converting fructose to HMF and/or its derivatives. In some of the foregoing embodiments, the one or more molecular sieves has a pore size between 2 Å to 10 Å. In some of the foregoing embodiments, the one or more molecular sieves has a pore size of 3 Å.

As used herein, the term "crude reaction mixture" includes, for instance, an unrefined or unpurified composition.

The term "compound intermediate" as used herein includes compounds that are formed from the starting material during a single reaction step or a multi-step process to form a product. In some instances, the intermediate is isolable. In some of the foregoing embodiments, the compound intermediate includes, for instance, a compound formed during any step in the process of synthesizing DMF. For instance, compound intermediates include but are not limited to the group consisting of HMF, BHMF, FMHF, BFMF, HMMF, FMF, FMMF, AMF, BAMF and HMTF. In alternative embodiments, the intermediate refers to a transient species.

In some of the foregoing embodiments, the reaction mixture is heated to reflux. The preferred temperature range will vary with the solvent and catalyst used. For instance, a THF-slurry with palladium on carbon as the catalyst, the preferred temperature is about 65° C. to 70° C., reflecting the boiling point of THF.

In some of the foregoing embodiments, the reaction temperature affects the amount of FMF in the reaction of fructose with formic acid. At higher temperatures, fructose is consumed and the reaction is complete in a shorter amount of time. On the other hand, at lower temperatures, the yield of the formate ester is increased in comparison to the yield at higher temperature; however, a longer reaction time is required. For example, at 150° C., 60-70% of HMF and a small amount of FMF were observed only after 2 hours, with the mole ratio of FMF to HMF approximately 8 to 2. In contrast, at 90° C., the selectivity to FMF increased to 90% yield, although longer reaction times (days) were required. Therefore, the reaction temperature should be selected in order to obtain satisfactory yields of the desired compound in a satisfactory amount of time. The water content of the reaction mixture also impacts the co-products formed in the reaction mixture, namely levulinic acid.

The time of the reaction will also vary with the reaction conditions and desired yield, but is generally about one to fifteen hours. In some of the foregoing embodiments, the reaction time is determined by the rate of conversion of the starting material. In some of the foregoing embodiments, the reaction mixture is heated for 10 to 20 hours. In some of the foregoing embodiments, the reaction mixture is heated for 1 to 10 hours. In some of the foregoing embodiments, the reaction mixture is heated for 1 to 5 hours. In some of the foregoing embodiments, the reaction mixture is heated for 1 to 3 hours. In some of the foregoing embodiments, the reaction mixture is heated for less than 2 hours.

In some of the foregoing embodiments, the reaction mixture can be cooled to room temperature and the insoluble catalyst removed by filtration. In some of the foregoing embodiments, isolation of the desired DMF product or any of the compound intermediates is achieved liquid-liquid extraction. For instance, this can be carried out by dilution of the reaction mixture with water and extraction with a suitable organic solvent, such as ether. In some of the foregoing embodiments, the extraction process is a continuous extraction process. In some of the foregoing embodiments, DMF is isolated by distillation. In some of the foregoing embodiments, a combination of methods is also suitable.

In some of the foregoing embodiments, the reaction mixture further includes an aprotic solvent.

The following examples are provided in order to illustrate but not to limit the invention.

EXAMPLES

Materials. All starting compounds are commercially available: D-fructose (Aldrich), 99% formic acid (Acros), 5% Pd on Activated Carbon (Aldrich), 5-(hydroxymethyl)furfural (Aldrich), benzyl formate (Aldrich) were used without further purification. $^1H$ and $^{13}C$ NMR spectra were acquired on Varian Unity 500 or Varian VXR 500. NMR spectra of the synthesized compounds were either compared to those of the standards (ref) or to the predicted spectra generated by Advanced Chemistry Development, Inc. (ACD/Labs) Software V9.07.

Example 1

Hydrogenation of HMF to BHMF

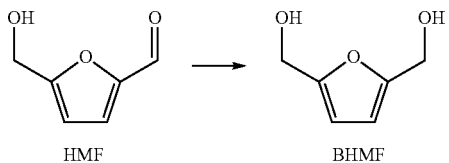

Figure 2:
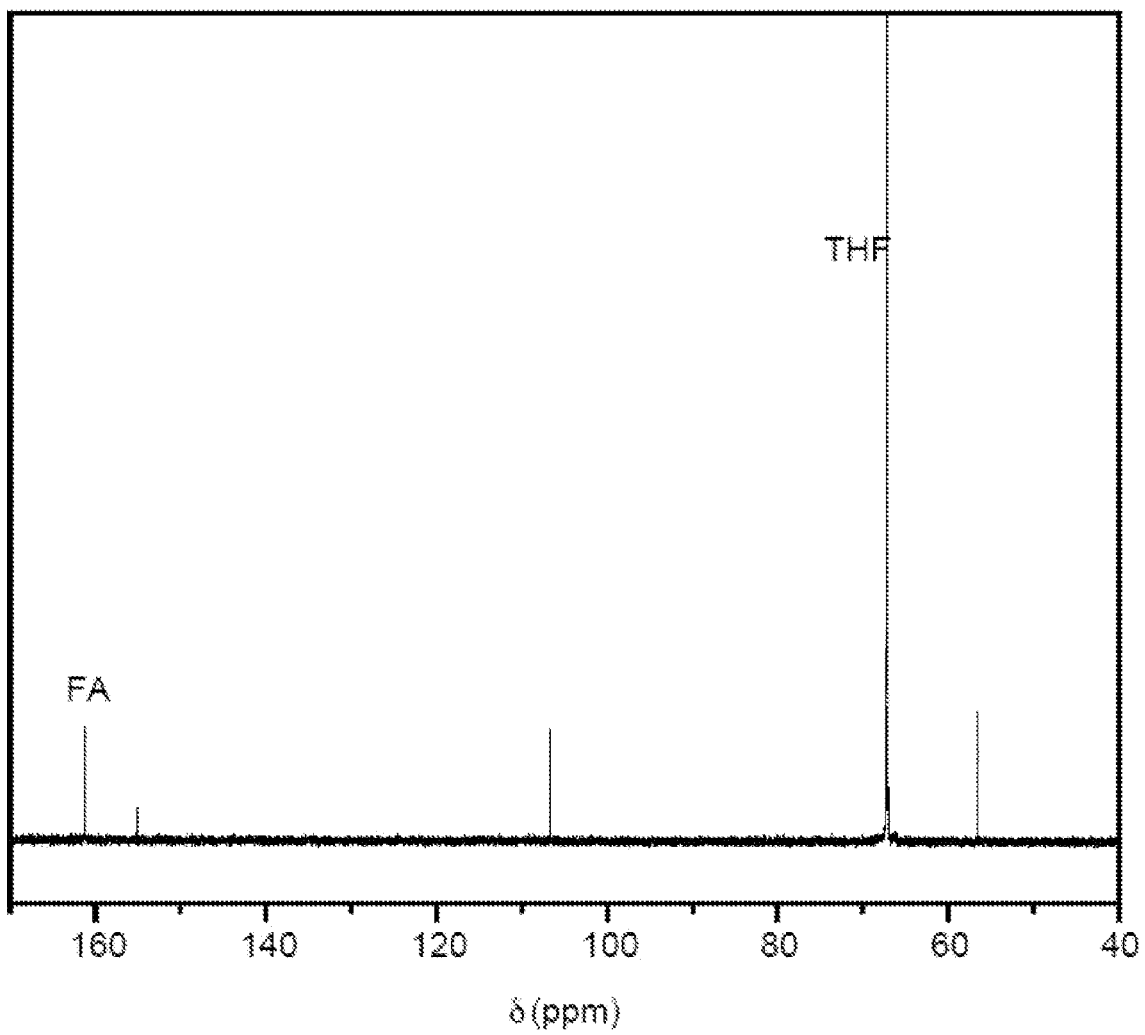
FIG. 2 is a $^{13}C$ NMR spectrum of a crude sample from the hydrogenation of HMF using FA and Pd/C catalyst.

This example demonstrates the reduction of HMF to BHMF with formic acid and palladium catalyst. To a 100-mL Schlenk flask, HMF (0.25 g, 2 mmol) was dissolved in THF (15 mL). Formic acid (0.31 mL, 8 mmol) and Pd/C (0.2 g) were subsequently added. The slurry was heated at reflux for 4 h. Pd/C was removed by filtration (catalyst recovered: 0.39 g). The colorless filtrate was concentrated under reduced pressure to yield light orange oil of BHMF (FIGS. 1 and 2). Yield: 0.24 g (94%).

Example 2

Synthesis of 2,5-bis[(formyloxy)methyl]furan, BFMF

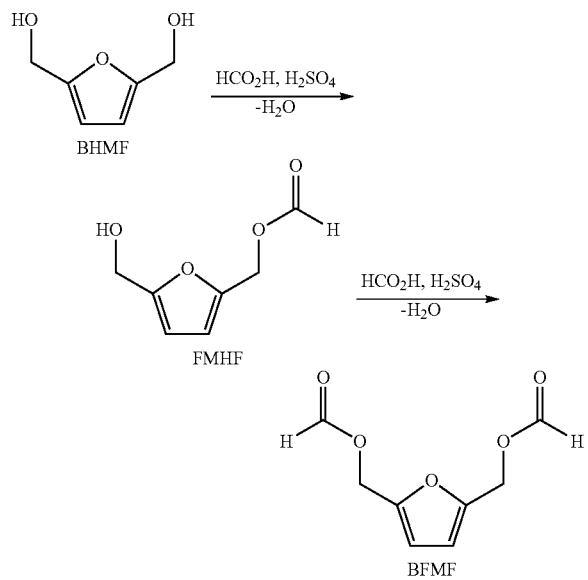

This example demonstrates that the conversion of BHMF to BFMF proceeds cleanly using formic acid and catalytic amounts of sulfuric acid. In a 50-mL round bottomed flask, BHMF (0.25 g, 2 mmol), formic acid (0.76 mL, 20 mmol), $H_2SO_4$ (6.9 µL, 0.13 mmol) were dissolved in THF (5 mL). The solution was heated at reflux for 15 h. The yellow solution was concentrated under reduced pressure, and the resulting oily residue was extracted with $CH_2Cl_2$ (10 mL×3). The organic layer was collected and the solvent was evaporated to yield BFMF as a brown oil. Yield: 0.32 g (87%). The intermediate FMHF, which was not isolated, was detected after 2 h (FIGS. 3 and 4).

$^1$H NMR for FMHF (500 MHz, DMSO-$d_6$): δ 8.23 (s, 1H, OCOH), 6.44 (d, $J_{H-H}$=3 Hz, 1H, furan ring proton), 6.24 (d, $J_{H-H}$=3.5 Hz, 1H, furan ring proton), 5.08 (s, 2H, $CH_2OCOH$), 4.36 (s, 2H, $CH_2OH$) (FIG. 1). $^{13}$C NMR for FMHF (125 MHz, DMSO-$d_6$): δ 161.54, 156.66, 148.38, 112.04, 108.10, 57.26, 55.91 (FIG. 4). HREI-MS: calculated for $C_7H_8O_4$ 156.04226, found 156.04292.

Figure 3:
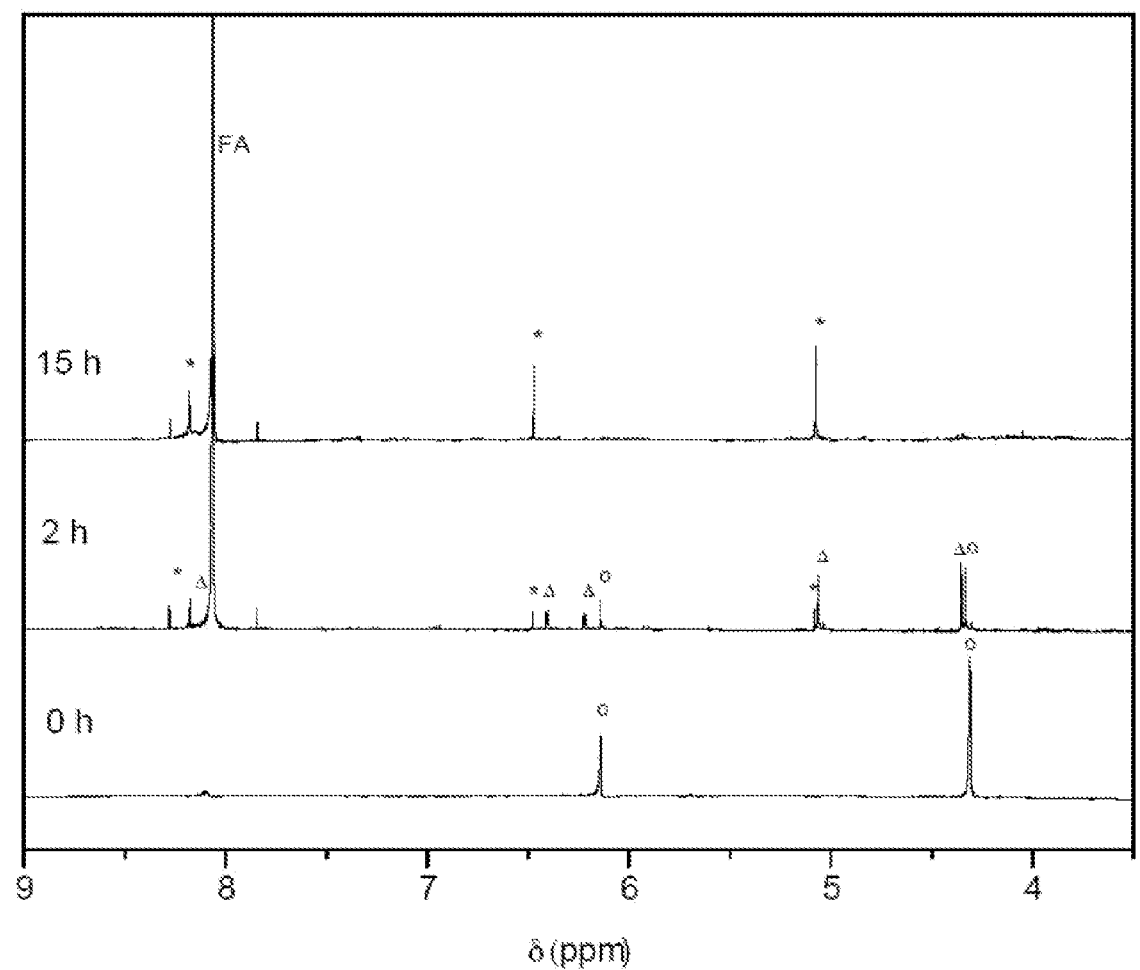
FIG. 3 is a $^1H$ NMR spectrum of a crude sample in DMSO-$d_6$ from the esterification of BHMF with FA. The labeling "o" in the spectrum represents BHMF, "Δ" represents FMHF, and "*" represents BFMF.
Figure 4:
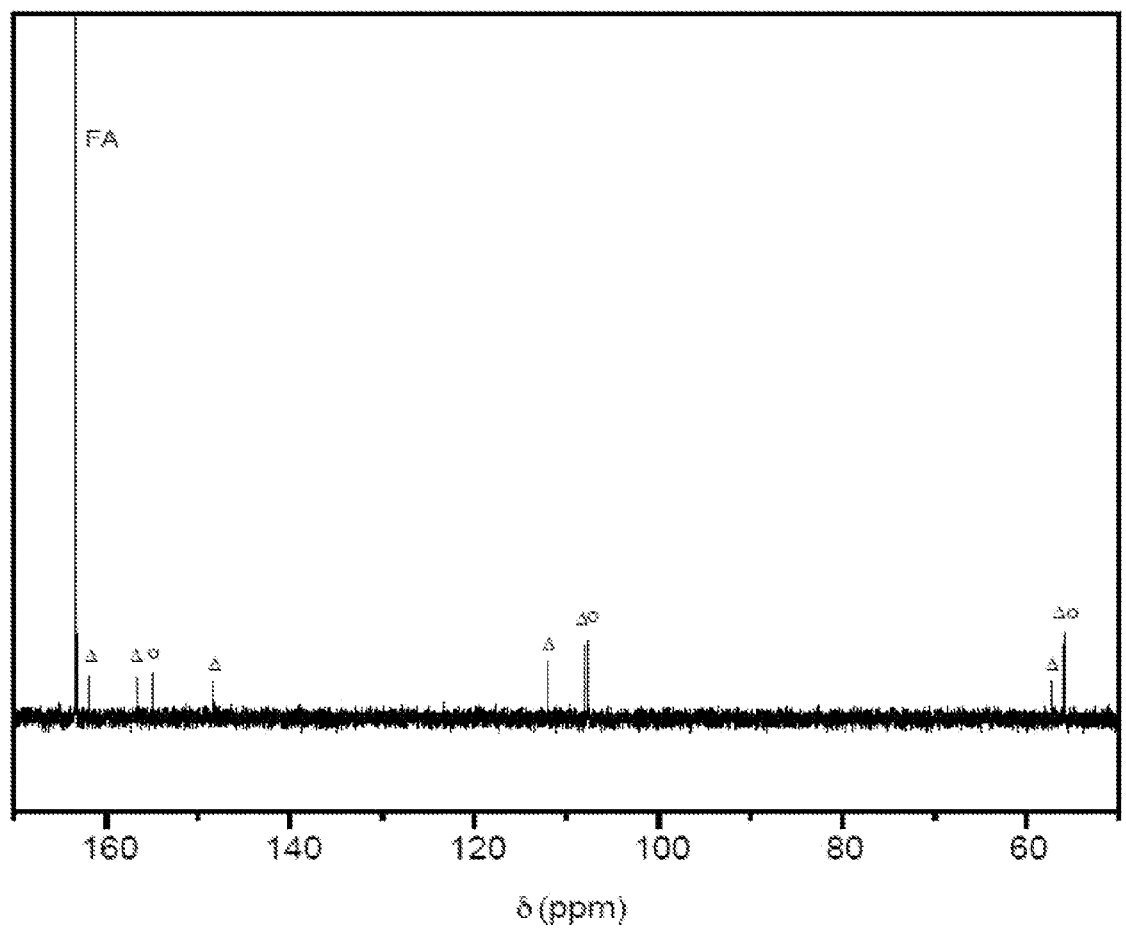
FIG. 4 is a $^{13}C$ NMR spectrum of a crude sample containing FMHF ("Δ") and BHMF ("o").
Figure 5:
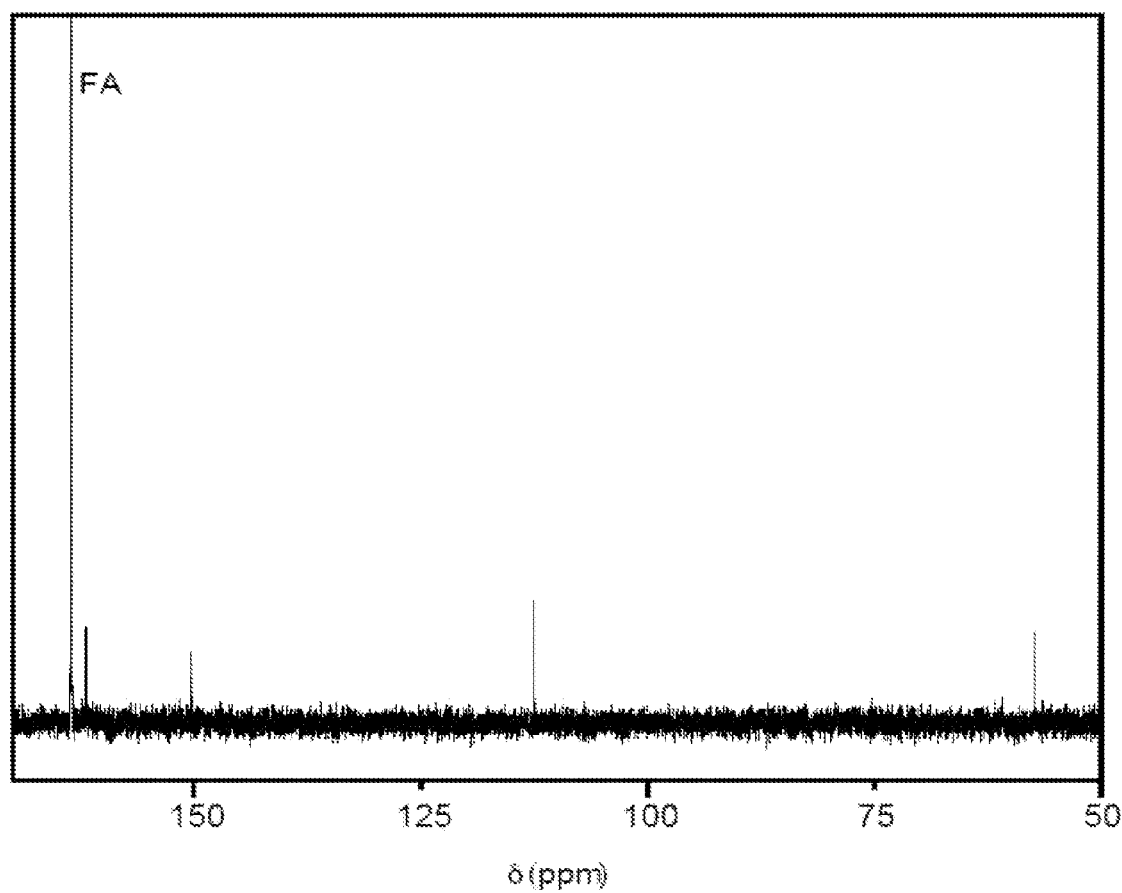
FIG. 5 is a $^{13}C$ NMR spectrum of a crude sample containing BFMF.
Figure 11:
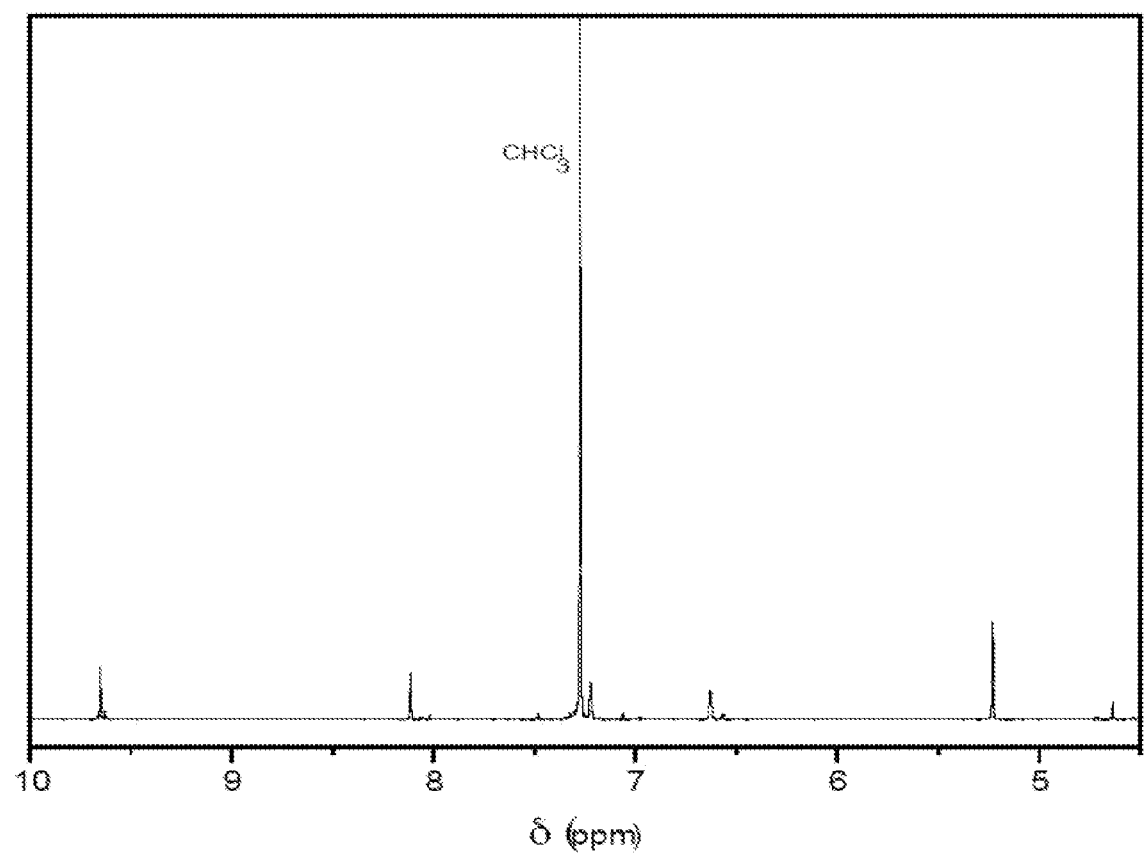
FIG. 11 is a $^1$H NMR spectrum of a crude sample of purified FMF in CDCl$_3$.
Figure 12:
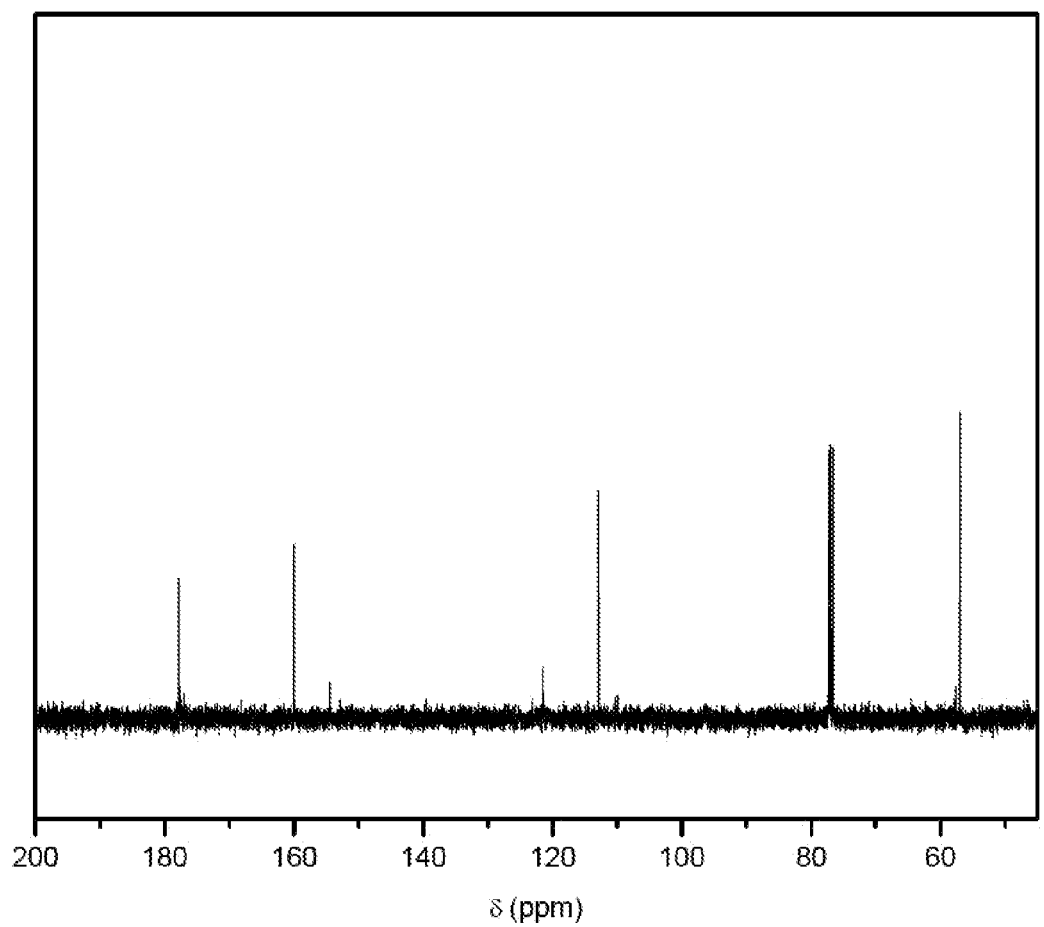
FIG. 12 is a $^{13}$C NMR spectrum of a crude sample of purified FMF in CDCl$_3$.

$^1$H NMR for BFMF (500 MHz, DMSO-$d_6$): δ 8.18 (s, 1H, OCOH), 6.48 (s, 1H, furan ring protons), 5.07 (s, 2H, $CH_2OCOH$) (FIGS. 3 and 11). $^{13}$C NMR for BFMF (125 MHz, DMSO-$d_6$): δ 161.95, 150.34, 112.48, 57.33 (FIGS. 5 and 12). HREI-MS: calculated for $C_8H_8O_5$ 184.03717, found 184.03761. Anal Calcd for $C_8H_8O_5$: C, 52.18; H, 4.38. Found: C, 51.97; H, 4.19.

Example 3

Hydrogenolysis of BHMF to DMF

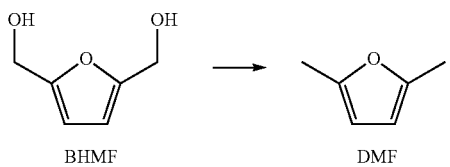

This example demonstrates that reduction of BHMF to DMF can be achieved with formic acid and a catalytic amount of base. A solution of BHMF (0.26 g, 2 mmol), formic acid (0.76 mL, 20 mmol), $H_2SO_4$ (13.8 µL, 0.26 mmol), THF (10 mL), and Pd/C (0.4 g) were heated at reflux for 15 h. $^1$H NMR spectroscopy of the solution confirmed a complete conversion of BHMF. Pd/C was removed by filtration (catalyst recovered: 0.38 g).

Example 4

Hydrogenolysis of BFMF to DMF

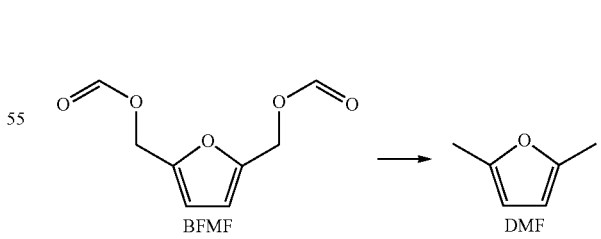

This example demonstrates decarboxylation of the diester, BFMF, with palladium catalyst. Pd/C (0.4 g) was added to a solution of BFMF (0.37 g, 2 mmol) in 10 mL THF. The suspension was stirred at reflux for 15 h. $^1$H NMR spectroscopy confirmed a complete conversion of BFMF. Pd/C was removed by filtration (catalyst recovered: 0.38 g).

Example 5

Hydrogenolysis of HMF to DMF

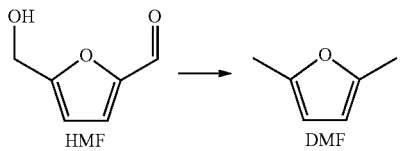

Figure 6:
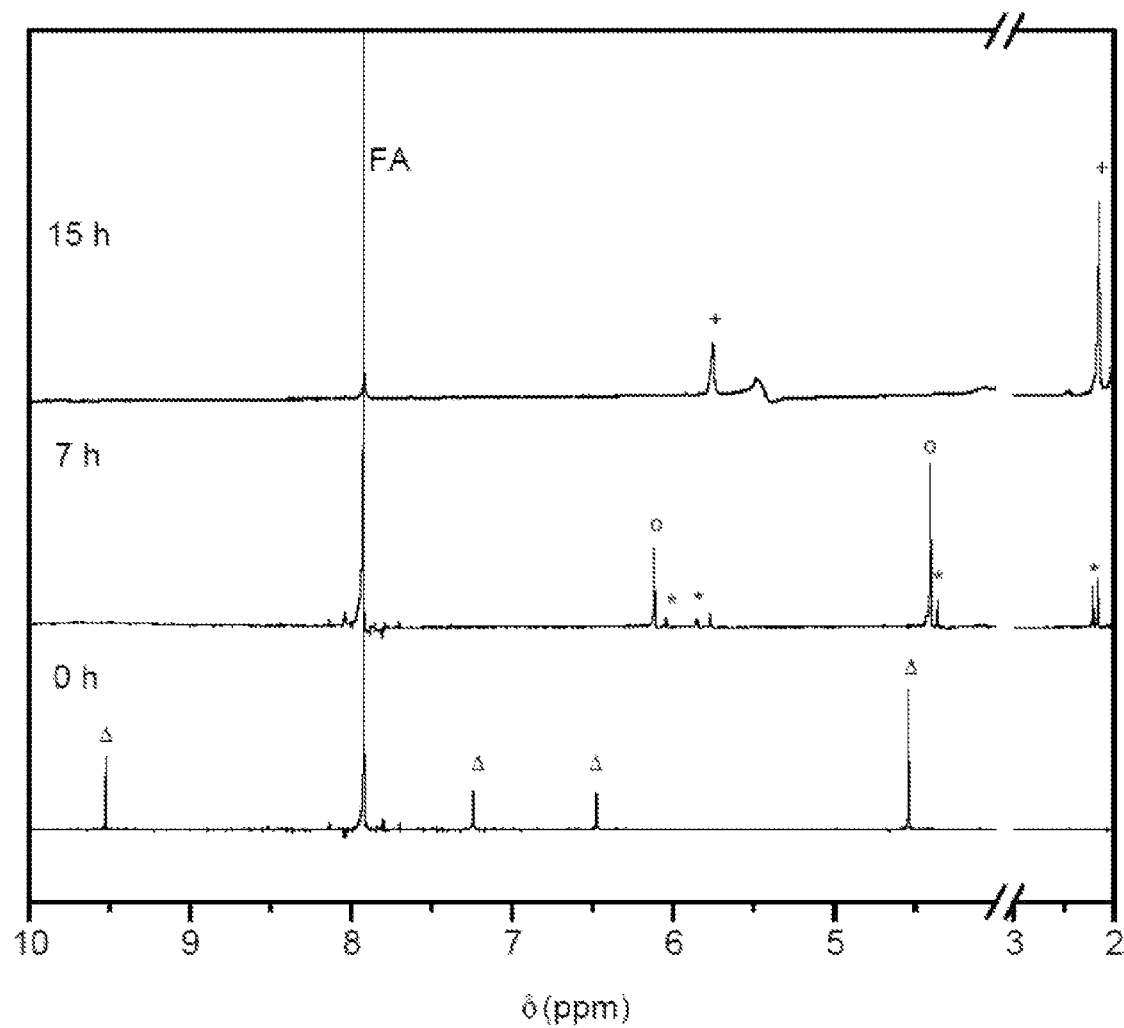
FIG. 6 is a $^1H$ NMR spectra of a crude sample in THF-$d_8$ from the hydrogenolysis of HMF using FA and Pd/C catalayst. The label of "Δ" represents HMF, "o" represents BHMF, "*" represents HMMF, and "+" represents DMF.
Figure 7:
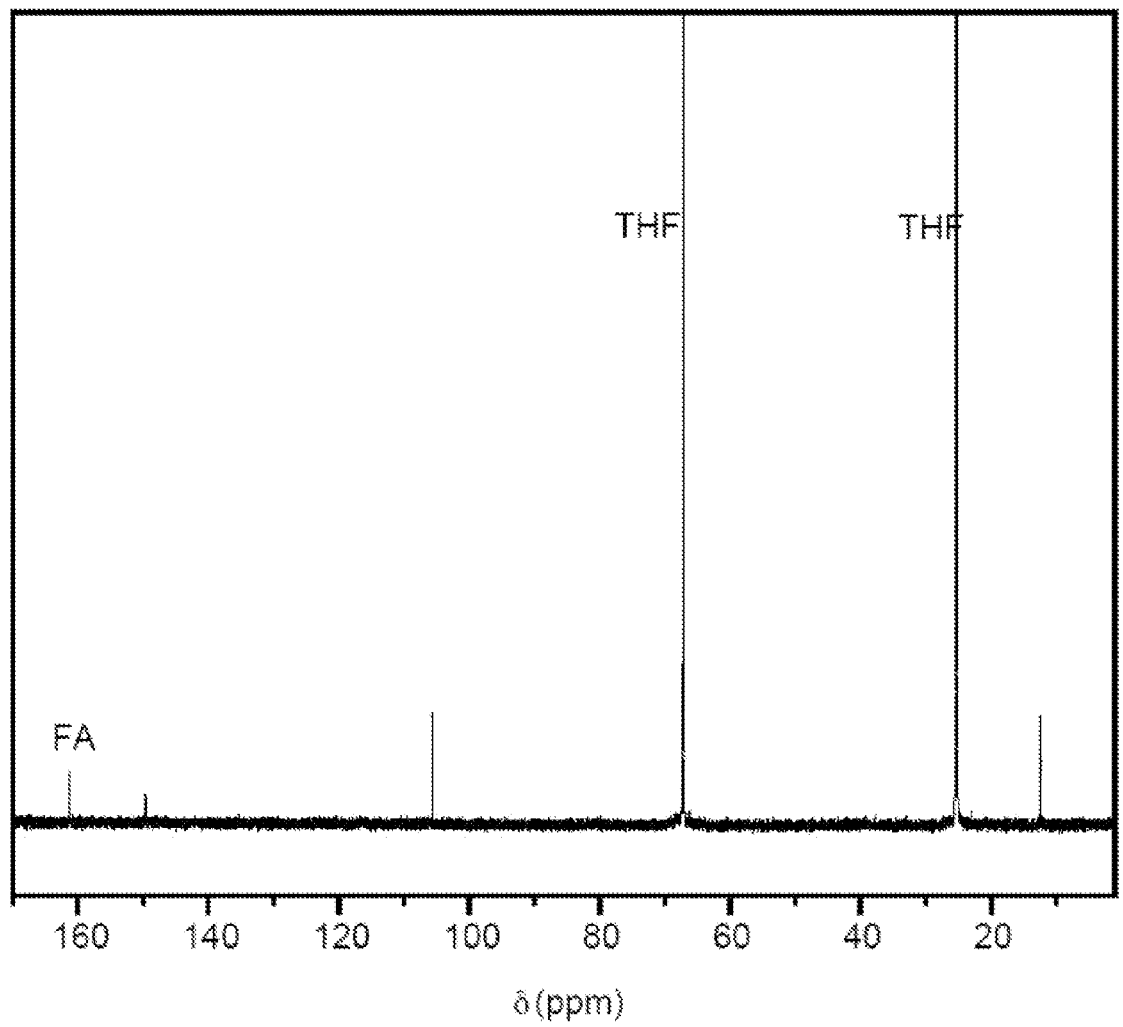
FIG. 7 is a $^{13}C$ NMR spectrum of a crude sample from the hydrogenolysis of HMF using FA and Pd/C catalyst.

This example demonstrates the one-pot conversion of HMF to DMF using formic acid as a hydrogen source and a deoxygenation agent. HMF (0.25 g, 2 mmol), formic acid (0.76 mL, 20 mmol), $H_2SO_4$ (13.8 μL, 0.26 mmol), THF (10 mL) and Pd/C (0.4 g) were stirred under reflux for 15 h. Pd/C was removed by filtration (catalyst recovered: 0.39 g). The solvent was removed by distillation at 90° C., and the residue of DMF was a pale yellow liquid. Isolated yield: 0.16 g (88%) (FIGS. 6 and 7).

NMR spectral monitoring of the reaction revealed signs assignable to HMMF as an intermediate, implicating a step-wise hydrogenolylsis of BHMF. The reaction pathway is described below:

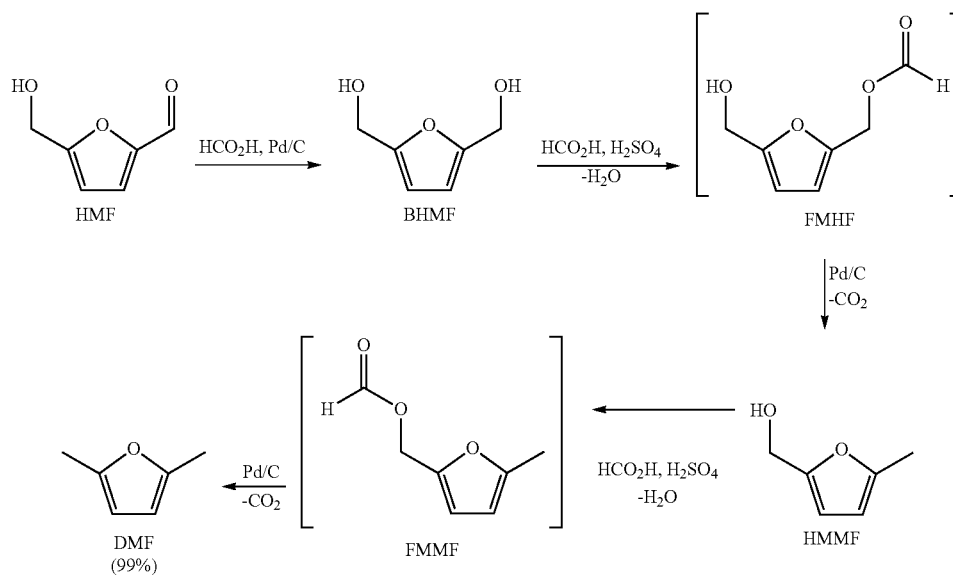

Example 6

Hydrogenolysis of Active Alcohols

This example demonstrates that a catalytic amount of a strong acid is necessary for hydrogenolysis of formate esters generated from furfuryl alcohol and benyl alcohol. Neither alcohol underwent hydrogenolysis in the presence of formic acid and Pd/C in THF. However, addition of catalytic amounts of sulfuric acid (0.065 equivalents/ROH) to such solutions resulted in clean conversions to 2-methylfuran and toluene.

Figure 8:
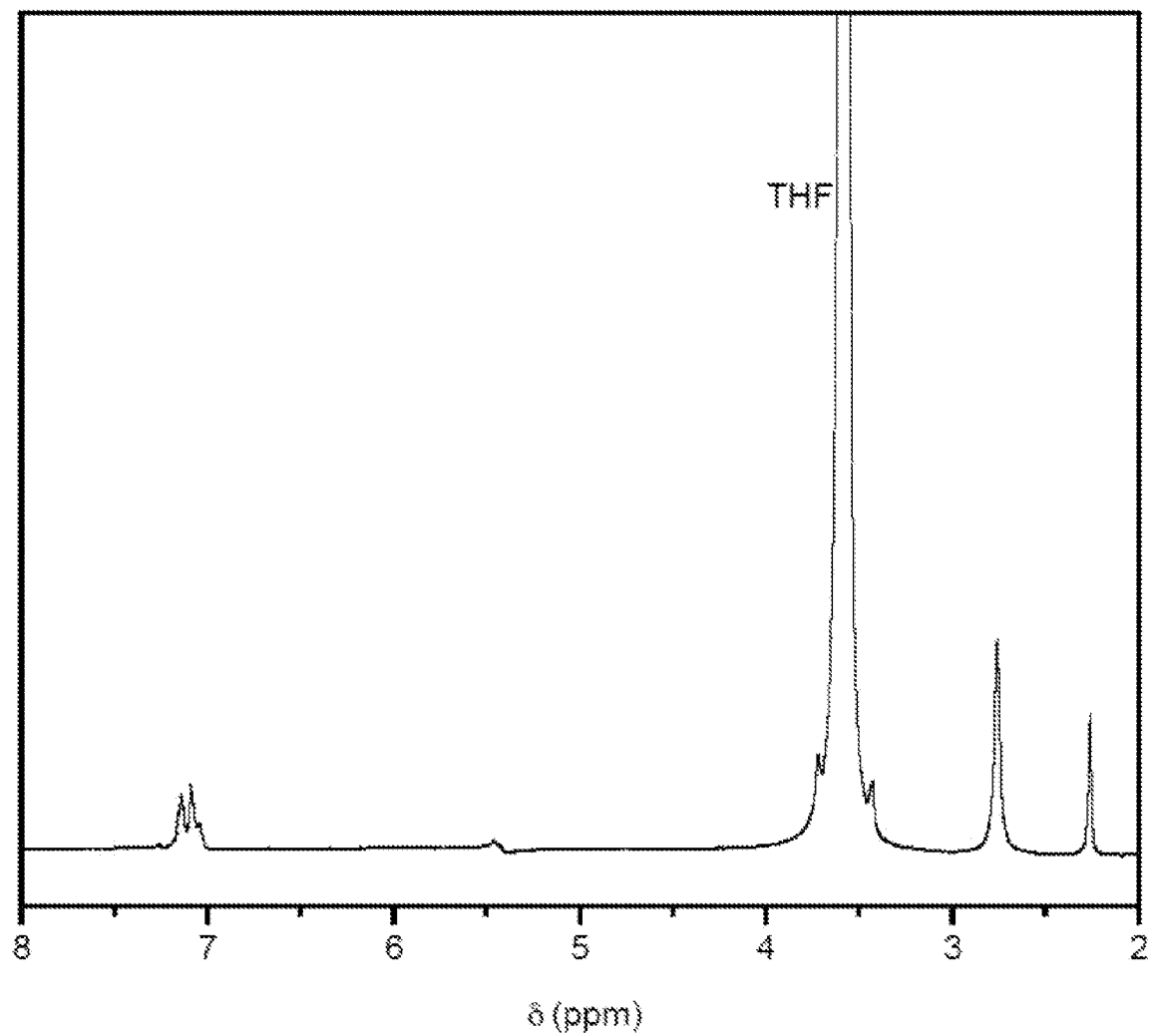
FIG. 8 is a $^1H$ NMR spectrum of a crude sample from the hydrogenolysis of benzyl alcohol using FA and Pd/C catalyst.
Figure 9:
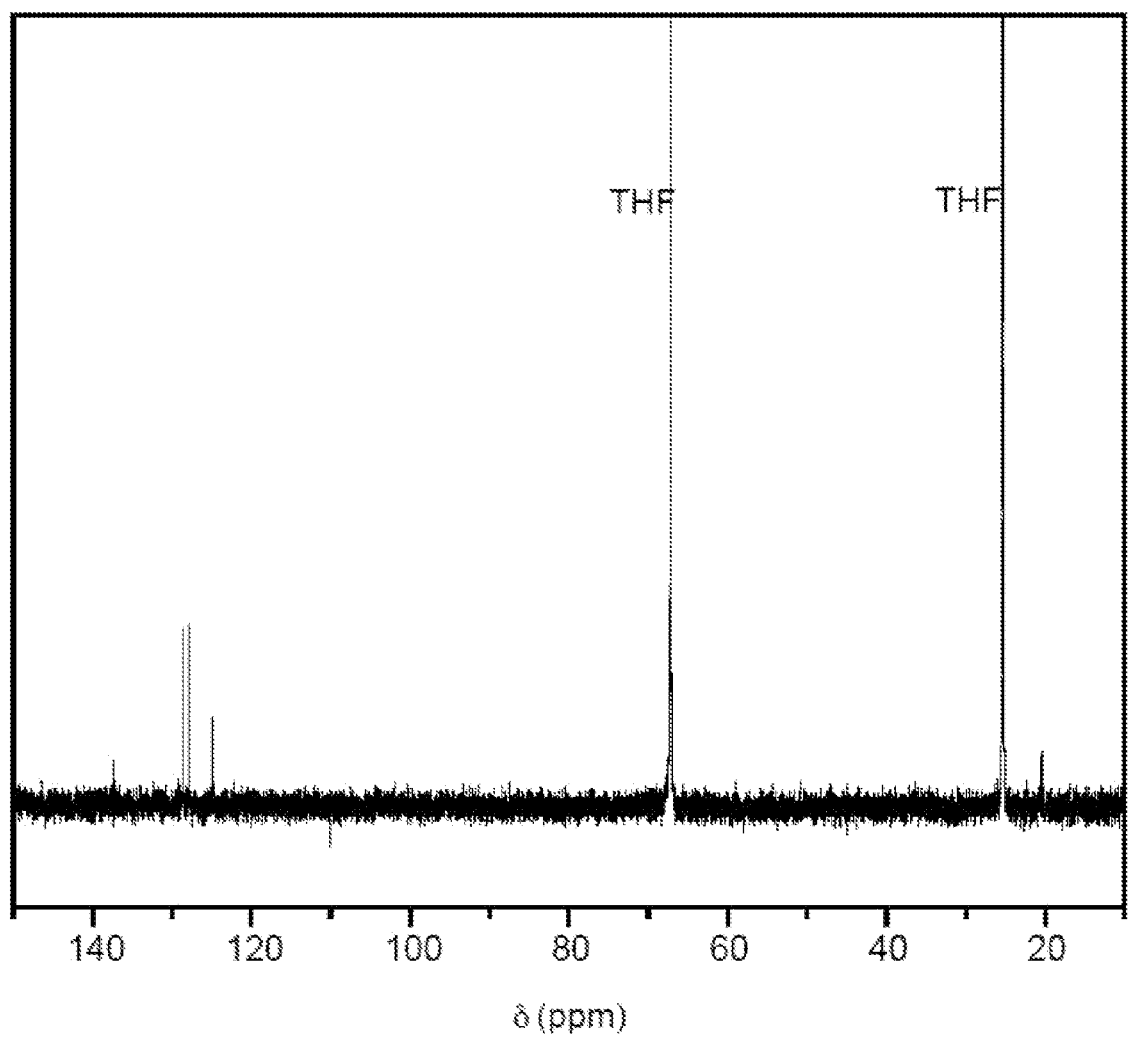
FIG. 9 is a $^{13}C$ NMR spectrum of a crude sample from the hydrogenolysis of benzyl alcohol using FA and Pd/C catalyst.

A solution of benzyl alcohol (2 mmol), formic acid (0.76 mL, 20 mmol), $H_2SO_4$ (6.9 μL, 0.13 mmol), THF (10 mL) and Pd/C (0.4 g) were heated to reflux for 15 h. $^1H$ and $^{13}C$ NMR spectra of the solution confirmed a quantitative conversion to its reduced product (FIGS. 8 and 9). Pd/C was removed by filtration (catalyst recovered: 0.39 g).

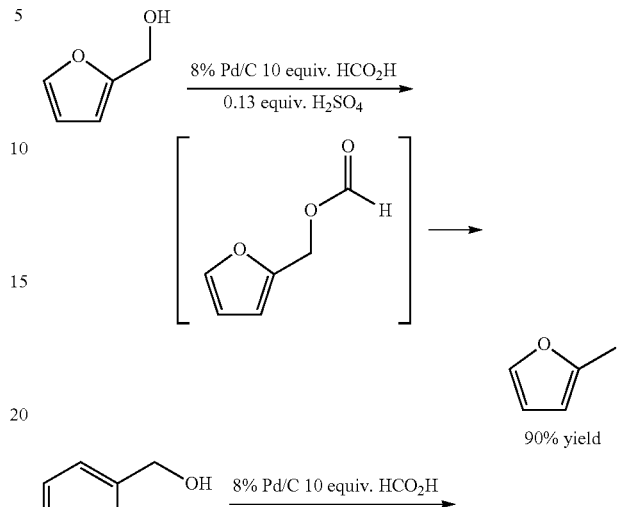

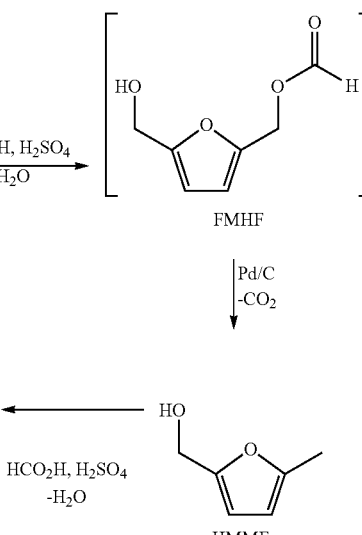

-continued

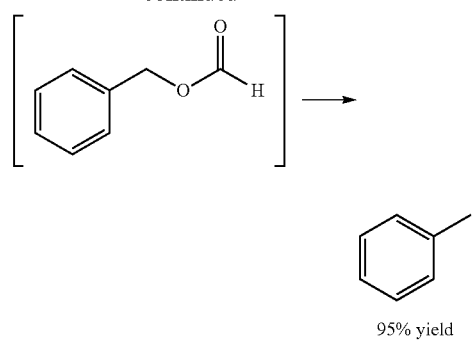

Example 7

Synthesis of FMF from HMF

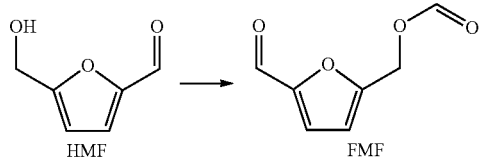

This example describes the esterification of HMF with formic acid and acetic anhydride. In a 50-mL Schlenk flask, formic acid (0.30 mL, 8 mmol) and acetic anhydride (0.82 mL, 8 mmol) were stirred at 0° C. (ice bath) under argon atmosphere for 1 h. A solution of HMF (0.25 g, 2 mmol) in 10 mL MeCN was added to the resulting colorless solution via syringe. Pyridine (0.032 mL, 0.4 mmol) was then added. The reaction mixture was stirred for 1 h at 0° C. and another 2 h at RT. Solvent and low boiling compounds were removed under vacuum to yield FMF as an orange oil. Yield: 0.28 g (90%).

Figure 13:
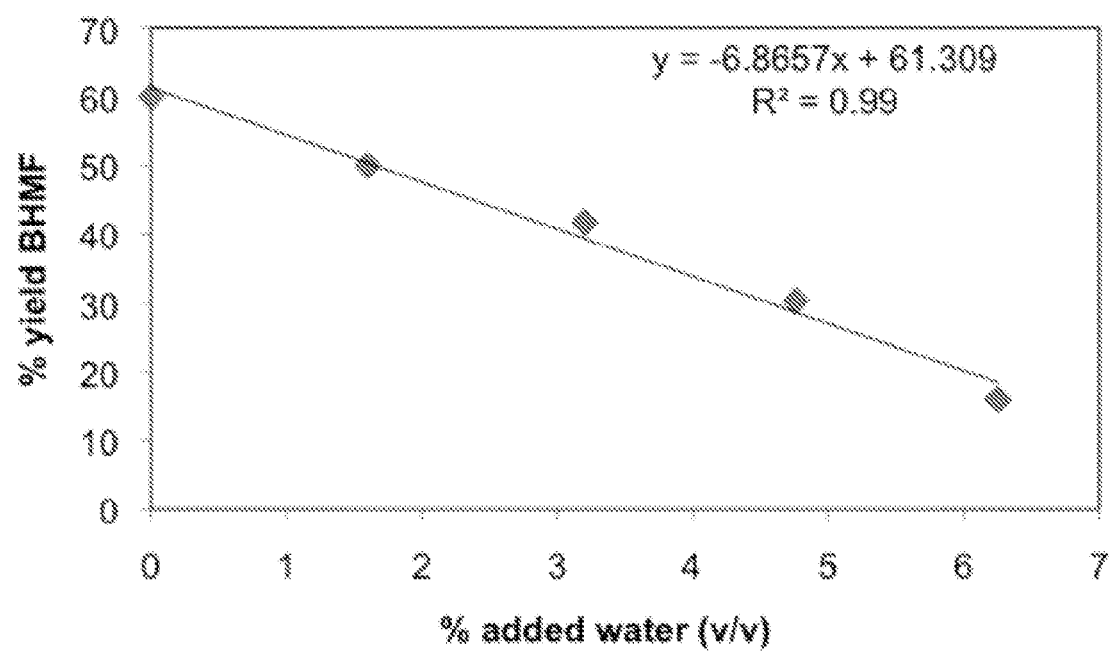
FIG. 13 illustrates the effect of water on reactivity of hydrogenation of HMF to BHMF with Pd/C catalyst. The reaction conditions are as follows: 0.2 mmol (0.25 g) HMF, 0.8 mmol (0.03 mL) FA, 4% Pd/C, 15 mL THF-H$_2$O, reflux for 2 hours.
Figure 14:
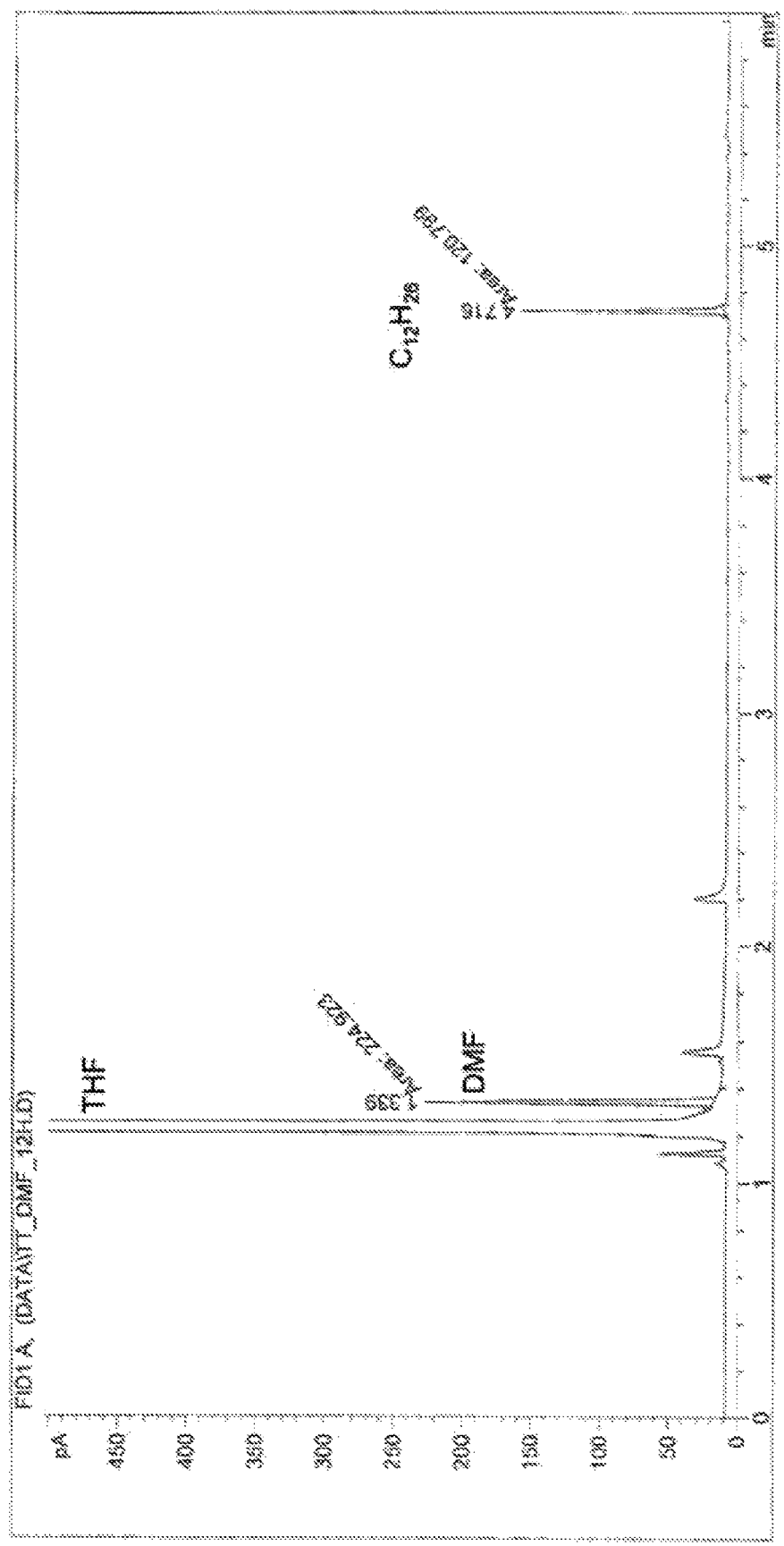
FIG. 14 illustrates a gas chromatography (GC) analysis of DMF.

$^1$H NMR for FMF (500 MHz, CDCl$_3$): δ 9.65 (s, 1H, OCOH), 8.11 (s, 1H, CH$_2$OCOH), 7.22 (d, $J_{H-H}$=3.5 Hz, 1H, furan ring proton), 6.63 (d, $J_{H-H}$=3.5 Hz, 1H, furan ring proton), 5.23 (s, 2H, CH$_2$OCOH) (FIG. 13). $^{13}$C NMR (125 MHz, CDCl$_3$): δ 178.48, 160.40, 154.95, 152.50, 122.76, 112.90, 56.93 (FIG. 14). HREI-MS: calculated for C$_7$H$_6$O$_4$ 154.02661, found 154.02658. Anal Calcd for C$_7$H$_{16}$O$_4$: C, 54.55; H, 3.92. Found: C, 54.11; H, 3.92.

Example 8

Formation of FMF from Fructose

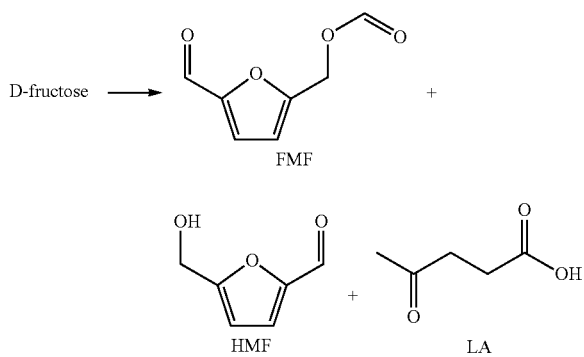

Figure 10:
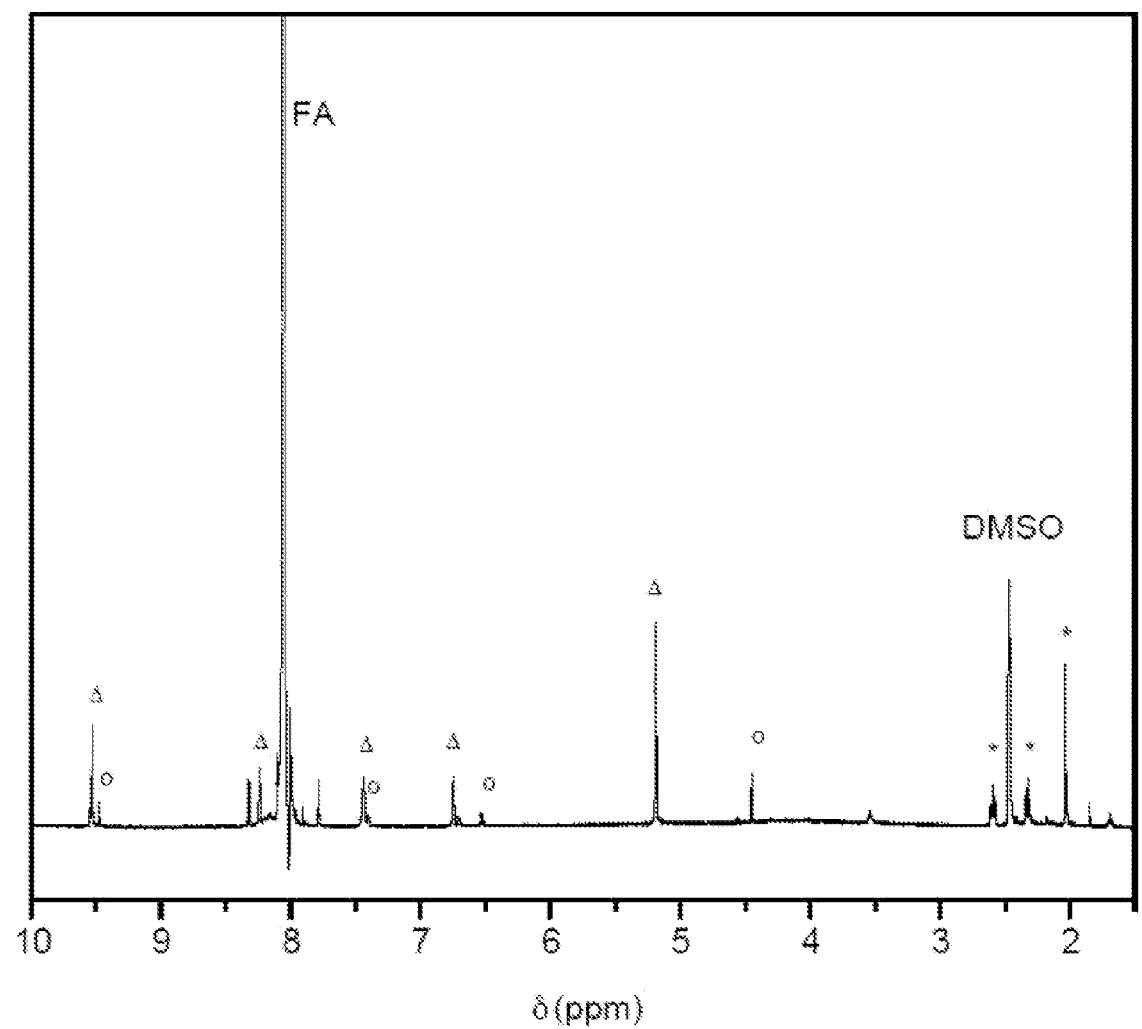
FIG. 10 is a $^1H$ NMR spectrum of a crude sample in DMSO-$d_6$ from the dehydration reaction of fructose and FA. The label of "Δ" represents FMF, "o" represents HMF, and "*" represents levulinic acid.

This example demonstrates the conversion of fructose to FMF using formic acid. Fructose (3.6 g, 20 mmol) and formic acid (10 mL) were added to a medium pressure reactor. The suspension was heated to 150° C. for 2 h. $^1$H NMR spectroscopy of the solution confirmed a conversion of HMF, FMF (60-70% yield total) and levulinic acid (30-40% yield) (FIG. 10).

Example 9

Hydrogenolysis of FMF to DMF

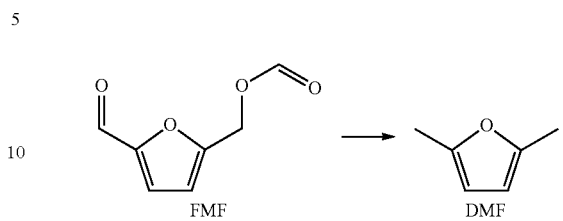

This example demonstrates the conversion of FMF to DMF using formic acid, catalytic amounts of sulfuric acid, and Pd/C catalyst. A solution of FMF (0.31 g, 2 mmol), formic acid (0.76 mL, 20 mmol), H$_2$SO$_4$ (13.8 μL, 0.26 mmol), THF (10 mL), and Pd/C (0.4 g) were heated at reflux for 15 h. $^1$H NMR spectroscopy of the solution confirmed a quantitative conversion of FMF. Pd/C was removed by filtration (catalyst recovered: 0.38 g).

Example 10

One-pot Synthesis of DMF from Fructose

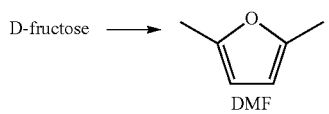

This example demonstrates a one-pot conversion of fructose to DMF and that formic acid can serve as both a reaction solvent and as a reagent. A suspension of fructose (3.6 g, 20 mmol) and formic acid (10 mL, 265 mmol) was stirred at 150° C. for 2 h. The resulting dark brown-colored solution was cooled to RT and diluted with THF (20 mL), followed by the addition of H$_2$SO$_4$ (0.138 mL, 2.6 mmol) and Pd/C (4 g). The solution was then stirred at 70° C. for further 15 h. Pd/C was removed by filtration (recovered: 3.9 g), and the filtrate was dilute with H$_2$O (20 mL), followed by extraction with ether (15 mL×3). The product was distilled at 90° C. Isolated yield of DMF: 1.1 mL (51%).

When fructose was treated with formic acid at lower temperatures (90° C.), the selectivity to FMF increased to 90% yield, although long reaction times (days) are required. The coproduct obtained in 30-40% yield was levulinic acid, depending on the water content of the FA (Note that the conversion of fructose to HMF generates three equiv of water). Levulinic acid is also a promising precursor for biofuels (Scheme 1). Without purification or isolation, the solution of ester FMF in FA was found to undergo hydrogenation and hydrogenolysis to DMF upon addition of a THF slurry of the Pd/C catalyst. The conversion is proposed to proceed through the formation of 2-hydroxymethyl-5-methylfuran intermediate (HMMF) and the monoformate ester (FMMF), which decarboxylates in the presence of Pd/C, yielding DMF (Since HMMF was observed in the reaction of HMF, it is reasonable that it will form under these conditions as well). Levulinic acid was unreactive under these reaction conditions and, thus, remained in the solution at the end of the reaction. Pd/C and formic acid were recovered by filtration and distillation.

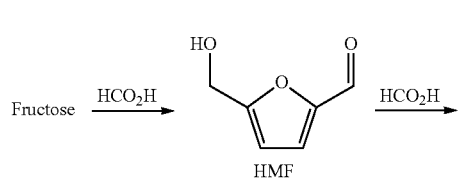

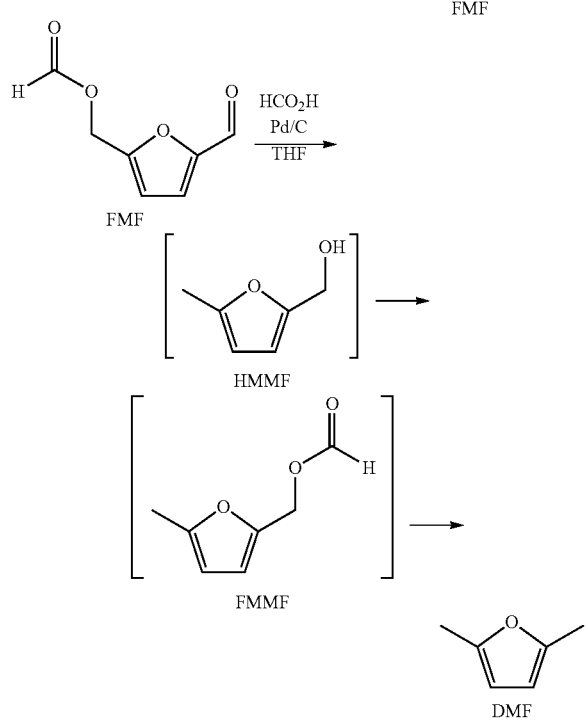

Example 11

Preparation of 5-[(acetoxy)methyl]furfural, AMF

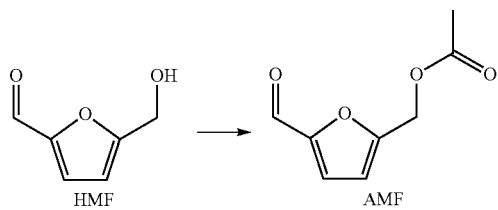

This example describes the conversion of HMF to AMF with acetic anhydride, and base. In a 50-mL Schlenk flask, pyridine (0.032 mL, 0.4 mmol) was added to a solution of HMF (0.25 g, 2 mmol) and acetic anhydride (0.28 mL, 3 mmol) in 10 mL of MeCN under argon atmosphere. The resulting orange solution was stirred at RT for 3 h. Solvent and volatile compounds were removed under vacuum to yield AMF as an orange oil. Yield: 0.30 g (89%).

Example 12

Preparation of 2,5-Bis[(acetoxy)methyl]furan, BAMF

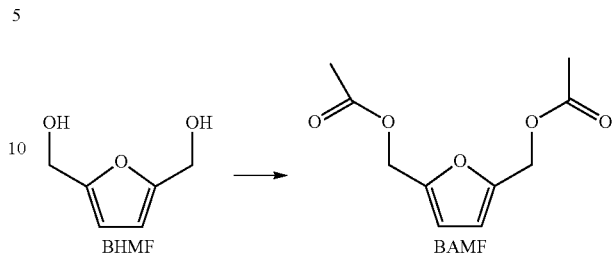

This example demonstrates the conversion of BHMF to BAMF with acetic anhydride, and base. In a 50-mL Schlenk flask, pyridine (0.5 mL, 6.24 mmol) was added to a solution of BHMF (1.0 g, 7.80 mmol) and acetic anhydride (2.20 mL, 23.4 mmol) in 20 mL MeCN under argon atmosphere. The resulting orange solution was stirred at RT for 3 h. Solvent and volatile compounds were removed under vacuum to yield BAMF as a brown oil. Yield: 1.50 g (92%).

Example 13

Hydrogenolysis of AMF to HMTF

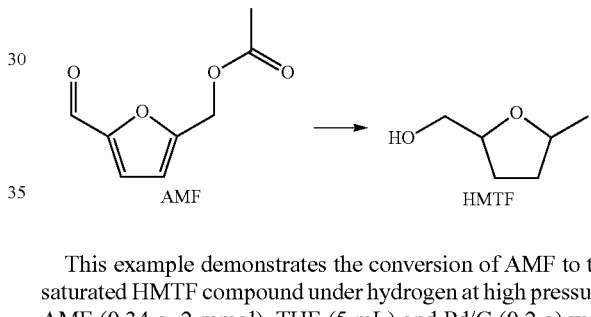

This example demonstrates the conversion of AMF to the saturated HMTF compound under hydrogen at high pressure. AMF (0.34 g, 2 mmol), THF (5 mL) and Pd/C (0.2 g) were charged to a high pressure reactor, which was pressurized to 1500 psi with $H_2$. The reaction was stirred at 90° C. for 24 h. $^1$H and $^{13}$C NMR spectroscopy of the solution confirmed a quantitative conversion of AMF. HMTF was obtained as a major product.

Example 14

Hydrogenolysis of BAMF to DTF

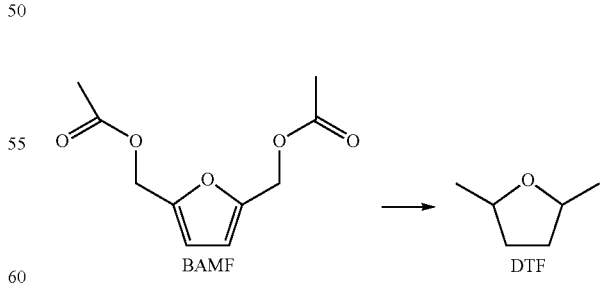

This example demonstrates the conversion of BAMF to the saturated DTF compound under hydrogen at high pressure. BAMF (0.42 g, 2 mmol), THF (5 mL) and Pd/C (0.2 g) were charged to a high pressure reactor, which was pressurized to 1500 psi with $H_2$. The reaction was stirred at 90° C. for 24 h. $^1$H and $^{13}$C NMR spectroscopy of the solution confirmed a quantitative conversion of BAMF. 2,5-dimethyltetrahydrofuran was obtained as a major product. Yield: DTF: 42% ($^1$H NMR).

Example 15

Hydrogenolysis of HMF to DTF

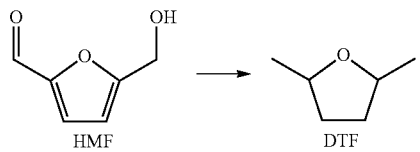

This example demonstrates the conversion of HMF to the saturated DTF compound under hydrogen at high pressure. HMF (0.25 g, 2 mmol), THF (5 mL), acetic acid (1.14 mL, 20 mmol), $H_2SO_4$ (13.8 µL, 0.26 mmol) and Pd/C (0.2 g) were charged to a high pressure reactor, which was pressurized to 1500 psi with $H_2$. The reaction was stirred at 90° C. for 24 h. $^1$H and $^{13}$C NMR spectroscopy of the solution confirmed a quantitative conversion of HMF. Yield DTF: 38% (1H NMR).

Example 16

Conversion of HMF into DMF using Formic Acid and Pd/C

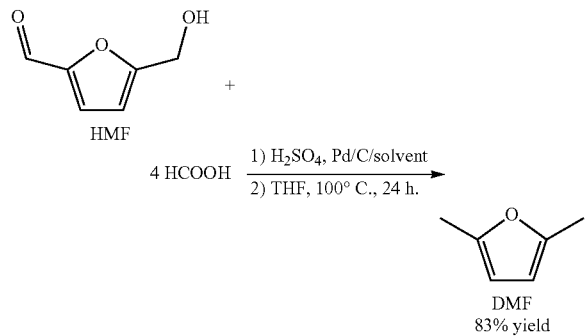

This example demonstrates that hydrogenolysis of HMF to DMF can be carried out with reduced amounts of formic acid in the presence of a strong acid catalyst. Specifically, the amount of formic acid was decreased from 10 equivalents (3.3× excess) to 4 equivalents (33% excess) and an amount of $H_2SO_4$ catalyst was added.

HMF, THF, formic acid (4 equiv.), $H_2SO_4$ (3 mol %, relative to HMF) and Pd/C (8 mol %) were stirred at 100° C. to yield DMF in 83% yield by gas chromatography relative to a dodecane standard.

Example 17

Reaction of 2,5-bis(acetoxymethyl)furan (BAMF) with $H_2$ and Pd/C

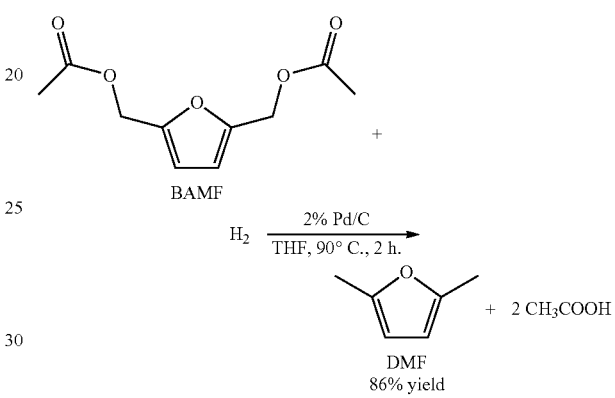

This example demonstrates the synthesis of DMF from the diester BAMF without over hydrogenation of the furan ring. In particular, the use of acetate esters is reported. Hydrogenolysis of BAMF was carried out under reduce $H_2$ pressure in the presence of Pd/C resulted in the formation of DMF.

BAMF (2 mmol), 2% Pd/C, and 5 mL THF was combined under hydrogen gas (<150 psi). The mixture was heated to 90° C. for 2 hours to form DMF in 86% yield, as determined by gas chromatography relative to a dodecane standard.

In related experiments, various substrates (2 mmol) was combined with 5 mL of THF and heated to 90° C. in the presence of a variety of conditions. The table below summarizes the results from acetate ester intermediates of various substrates.

| Substrate | Carboxylic acid | Conditions | Time (h) | Exclusive Product |
| --- | --- | --- | --- | --- |
| 2-Acetoxymethyl-furan | — | Pd/C | 15 | NR |
| | | $H_2$ (1500 psi) Pd/C (4% wt) | 24 | |

| Substrate | Carboxylic acid | Conditions | Time (h) | Exclusive Product |
|---|---|---|---|---|
| 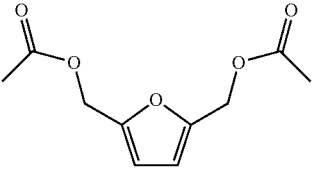<br>2,5-Bis(acetoxy-methyl)furan | — | Pd/C | 20 | NR |
| | | $H_2$ (500 psi)<br>Pd/C (4% wt) | 2 | 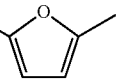 |
| | | | 12 | 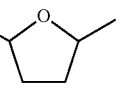<br>(2 isomers) |
| | | $H_2$ (500 psi)<br>Ru/C (4% wt) | 20 | 20 h, <5% conversion |
| | | $H_2$ (500 psi)<br>Pd/$Al_2O_3$ (4% wt) | 20 | 20 h, <5% conversion |
| | | HCOOH (10 eq.)<br>Pd/C | 20 | 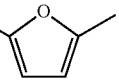 |

In addition, furfuryl alcohol and HMF was treated with 10 equivalents of acetic acid under a variety of hydrogenation conditions as shown in the chart below. These conditions result in the hydrogenation of the furan ring.

| | | | | |
|---|---|---|---|---|
| 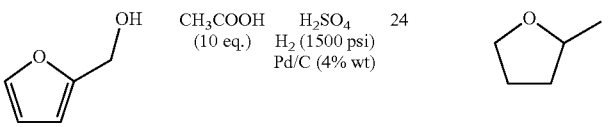<br>Furfuryl alcohol | $CH_3COOH$ (10 eq.) | $H_2SO_4$<br>$H_2$ (1500 psi)<br>Pd/C (4% wt) | 24 | 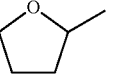 |
| 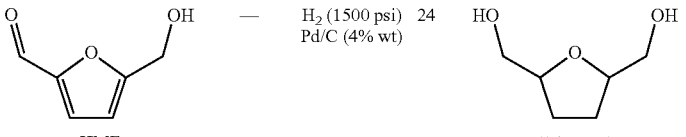<br>HMF | — | $H_2$ (1500 psi)<br>Pd/C (4% wt) | 24 | 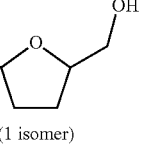<br>(1 isomer) |
| | $CH_3COOH$ (10 eq.) | $H_2SO_4$<br>$H_2$ (1500 psi)<br>Pd/C (4% wt) | 24 | 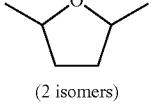<br>(2 isomers) |
| | | $H_2$ (1500 psi)<br>Pd/C (4% wt) | 24 | 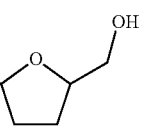<br>(1 isomer) |

Example 18

Conversion of HMF to DMF via the BAMF Intermediate

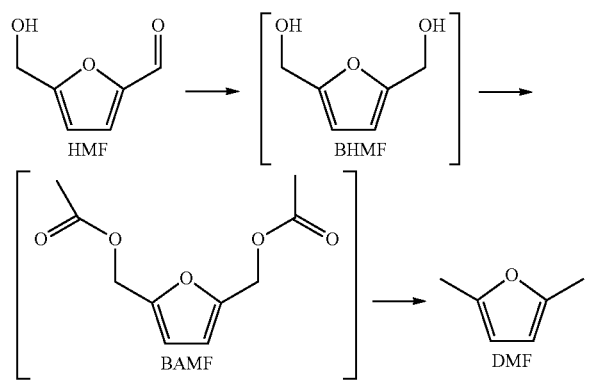

This example describes the conversion of HMF to DMF via a diester intermediate. First, HMF is converted to BHMF by combining HMF with Pd/C (2 mol %) in THF, and stiffing under pressure with $H_2$ (<150 psi) to form the hydrogenated bis-alcohol product, BHMF. BHMF is combined with acetic acid (10 equiv.) and $H_2SO_4$ (0.6 equiv) to form the diester, BAMF. Hyrdogenolysis of the diester, BAMF, is carried out under pressure with $H_2$ (<150 psi) using the same Pd/C to form the product DMF.

Example 19

Conversion of D-Fructose to HMF using Various Acids

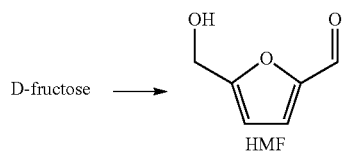

This example demonstrates the dehydration of D-fructose to HMF using various acids. D-fructose (3.6 g) was combined with 10 mol % acid and 10 mL of solvent. The reaction mixture was heated at 100° C. or 150° C. The % yield of HMF was determined by $^1$H NMR. The exact reagents, reaction conditions and results are summarized in the table below.

| Entry | Acid | Media | Temp (° C.) | Time (h) | % Yield HMF | Others |
|---|---|---|---|---|---|---|
| 1 | $H_2SO_4$ | $H_2O$ | 100 | 20 | 35 | LA (24%) FA (9%) Humins |
| 2 | $H_2SO_4$ | DMSO | 100 | 5 | 93 | LA (4%) FA (3%) |
| 3 | HCOOH | DMSO | 150 | 8 | 99 | — |
| 4 | Oxalic acid | DMSO | 150 | 6 | 99 | — |
| 5 | $CH_3COOH$ | DMSO | 150 | 15 | 99 | — |
| 6 | HCOOH | DMSO | 150 | 6 | 99 | — |

From the results, it is observed that reaction catalyzed by sulfuric acid in DMSO was significantly accelerated as compared to the reaction carried out in water. Specifically, at 100° C. quantitative conversion of D-fructose was achieved after only 5 h in DMSO-sulfuric acid, whereas only 70% of D-fructose was converted in water-sulfuric acid after 20 h. Furthermore, side reactions were significantly diminished in DMSO, where the yield of HMF was calculated at 93%. In water, the yield of HMF was 35% and side reactions resulted in the formation of LA, FA and insoluble humins, which account for about 35%. Entry 6 was carried out in 1 mL of DMSO.

This example also demonstrates that formic add may be used in place of sulfuric acid as the catalyst for the conversion of D-fructose into HMF. Under comparable conditions, formic acid ($pK_a$=3.75) is a slower catalyst than sulfuric acid ($pK_a$=−3). For instance, a solution of D-fructose and 10% formic acid in DMSO at 150° C. quantitatively converted D-fructose into HMF (99%) after 8 h (entry 3). Since the reaction was carried out in DMSO, we did not observe the formation of LA or humins (black solids). Furthermore, formic acid is not a mineral acid, so its salts do not accumulate in the reaction mixture. Hence, we note the exceptionally clean conversion of D-fructose to HMF when using formic acid-DMSO conditions. Other organic acids such as oxalic acid ($pK_a$=1.27) and acetic acid ($pK_a$=4.76) were also effectively capable of catalyzing the HMF formation (entries 4-5).

Thus, this example demonstrates the advantage of using DMSO as a medium for conversion of D-fructose to HMF. Using sulfuric acid as a catalyst, DMSO significantly accelerates the formation of HMF compared to reactions in water. Furthermore, side reactions are significantly diminished in DMSO. These side reactions include the formation of levulinic acid and formic acid. We also demonstrated that formic acid can be used in place of sulfuric acid as the catalyst for the conversion of D-fructose into HMF. Under comparable conditions, formic acid is a slower catalyst than sulfuric acid. Formic acid is however interesting because it is "greener" with respect to its formation (from $CO_2$) and it is not a mineral acid, so its salts do not accumulate.

Example 20

Conversion of HMF to BHMF using Ir Catalysts

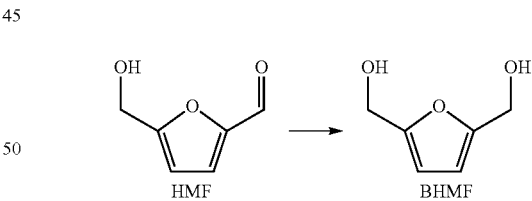

This example demonstrates the use of various transfer hydrogenation Ir catalysts and formic acid as the hydrogen donor in the hydrogenation of HMF to BHMF.

The different catalysts vary in terms of their stabilities toward formic acid. To test the stability of the catalyst, the iridium catalyst and formic acid was combined in a 1:10 ratio in 1 mL $d_6$-DMSO. Catalyst decomposition was monitored by $^1$H NMR at 20° C. Cp*Ir(TsDPEN) was found to have a half life of about 2 hours whereas Cp*Ir(NHCPh$_2$C$_6$H$_4$) and CP*IrH(TsDACH-H) have half-lives of minutes after exposure to formic acid.

The catalysts were evaluated in the transfer hydrogenation of HMF. HMF (0.25 g), was combined with DMSO (3 mL) and 0.1-1% of an iridium based catalyst. Formic acid in DMSO was dispensed via a syringe pump at a rate of 2 mL/h to minimize catalyst decomposition. The reaction of HMF and formic acid occurred quantitatively in the presence of 0.1-1% catalyst at 40° C. in 1-4 hours. Methanol, which is traditionally employed for transfer hydrogenation catalysis, was also evaluated as a hydrogen donor (entry 3). Combining HMF (2 mmol), catalyst and methanol (5 mL) results in a much longer reaction time of 16 hours to produce a 99% yield of BHMF. The results are summarized in the table below. This experiment shows that formic acid is a highly effective hydrogen donor.

| Entry | Catalyst | % cat. | H-donor | Time (h) | % yield BHMF |
|---|---|---|---|---|---|
| 1 | Cp*Ir(TsDPEN) | 0.5 | HCO$_2$H | 2 | 99 |
| 2 | Cp*Ir(TsDPEN) | 0.1 | HCO$_2$H | 4 | 70 |
| 3 | Cp*Ir(TsDPEN) | 1 | NaOH | 16 | 99 |
| 4 | Cp*IrH(TsDACH-H) | 0.5 | HCO$_2$H | 1 | 99 |
| 5 | Cp*Ir(NHCPh$_2$C$_6$H$_4$) | 0.5 | HCO$_2$H | 1 | 99 |

Example 21

Conversion of D-fructose to BHMF via HMF using Ir Catalysts

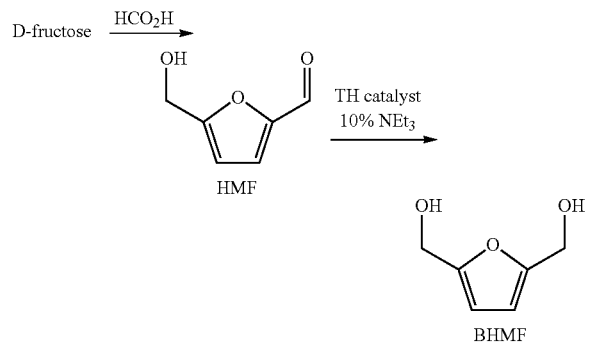

This example demonstrates the use of formic acid and Ir catalysts in the hydrogenation of HMF prepared in situ from D-fructose. In view of examples 19 and 20, the conversion of D-fructose into BHMF via a one-pot process was demonstrated.

In a two-step, one-pot process, formic acid served initially as an acid catalyst for the dehydration step (a)nd subsequently as an H$_2$ donor for the hydrogenation. D-fructose (20 mmol), formic acid (2 mmol, 10 mol %), DMSO (5 mL) were combined and stirred at 40° C. to form HMF. An iridium based catalyst (0.5-1%) was then added to the reaction mixture catalyze the formation of BHMF. The amount of formic acid present in the reaction mixture (10 mol % based on fructose) appeared to be incompatible with the selected catalysts and led to a decrease in activity in the hydrogenation step to BHMF. The addition of a base is needed to neutralize the formic acid prior to addition of the catalyst.

The HMF-formic acid solution was neutralized with base (10 mol % based on fructose, 1 equivalent to formic acid), prior to addition of the iridium catalyst. Then the solution was stirred at 40° C. for 5 minutes before adding a solution of formic acid (2 mmol) in DMSO (2 mL) at a rate of 1 mL/h. Catalysis proceeded efficiently after neutralizing the formic acid prior to addition of the catalyst. The results are summarized in the table below.

| Entry | Catalyst | % cat. | Base | Time (h) | % yield BHMF |
|---|---|---|---|---|---|
| 1 | Cp*Ir(TsDPEN) | 1 | — | 12 | 80 |
| 2 | Cp*IrH(TsDACH-H) | 1 | — | 12 | NR |
| 3 | Cp*Ir(NHCPh$_2$C$_6$H$_4$) | 1 | — | 6 | 80 |
| 4 | Cp*Ir(TsDPEN) | 0.5 | NaOH | 2 | 99 |
| 5 | Cp*Ir(TsDPEN) | 0.5 | NEt$_3$ | 2 | 99 |
| 6 | Cp*Ir(TsDPEN) | 0.05 | NEt$_3$ | 10 | 83 |
| 7 | Cp*IrH(TsDACH-H) | 0.5 | NEt$_3$ | 2 | 63 |
| 8 | Cp*Ir(NHCPh$_2$C$_6$H$_4$) | 0.5 | NEt$_3$ | 2 | 77 |

In the absence of base, a decrease in catalytic activity is observed (entry 1-3). However, upon addition of an equivalent of NaOH or triethylamine, the conversion to BHMF proceeded efficiently and was complete within 2 hours (entries 4-7). A variety of other bases could be used in principle. Entry 6 demonstrates that the catalyst loading can be reduced by an order of magnitude to 0.05% while still resulting in an 83% yield of BHMF.

Example 22

Effects of Carboxylic Acid on the Generation of HMF from Fructose

This example compares the effects of using different carboxylic acids on the rate of conversion of fructose to HMF in various carboxylic acids. The experiment calculates the half-life of the acid used in the reaction.

The reaction conditions involved combining fructose (0.036 g, 0.2 mmol), 10 mol % acid, 1 mL DMSO-d$_6$ and heating the reaction mixture to a temperature of 100° C. The different acids compared were formic acid, oxalic acid and acetic acid. The concentration of HMF was quantified over the course of the reaction by $^1$H NMR using 1,3,5-trimethoxybenzene as an internal standard.

Figure 15:
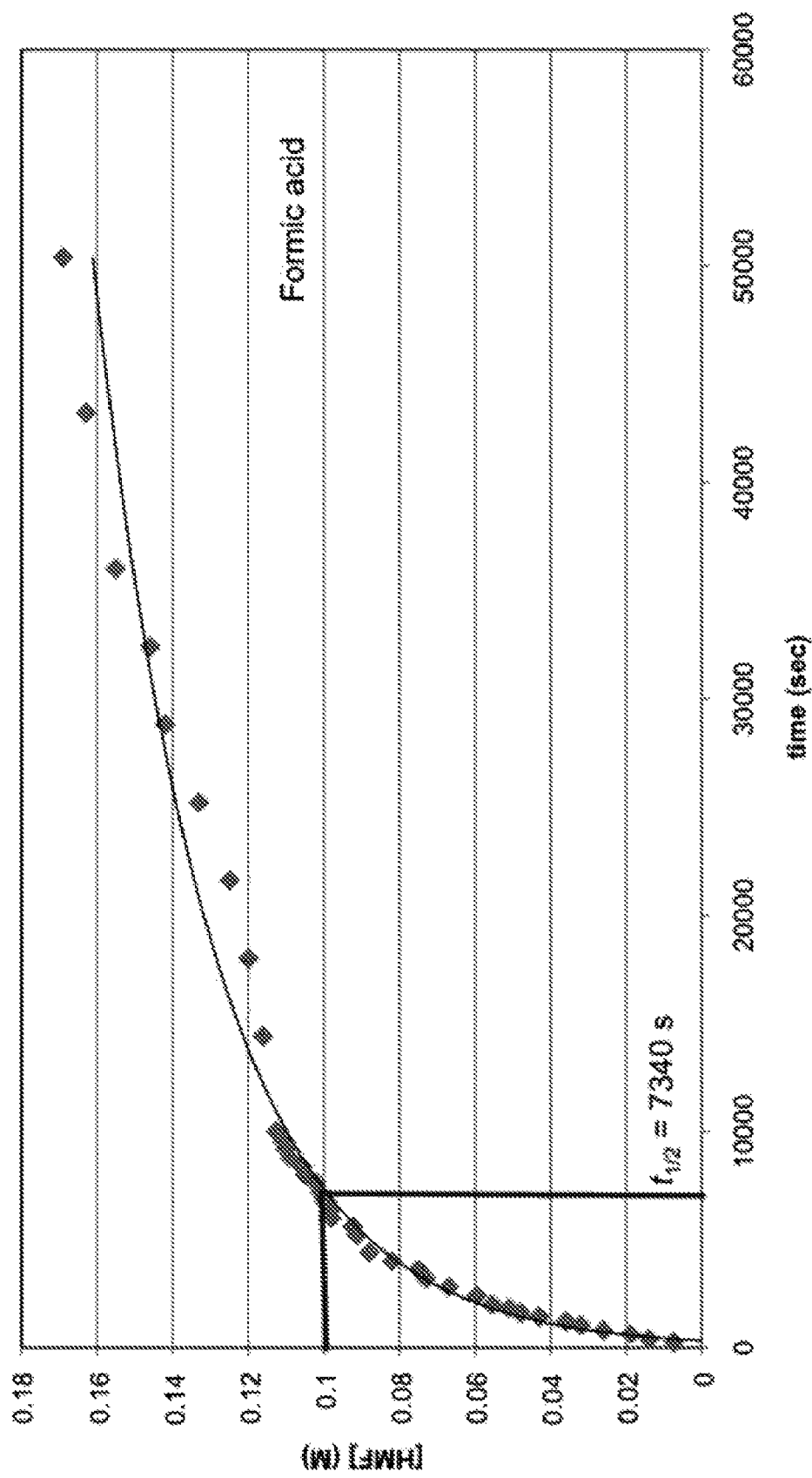
FIG. 15 shows the concentration of HMF generated from fructose over time in formic acid (15A), oxalic acid (15B), and acetic acid (15C).
Figure 15:
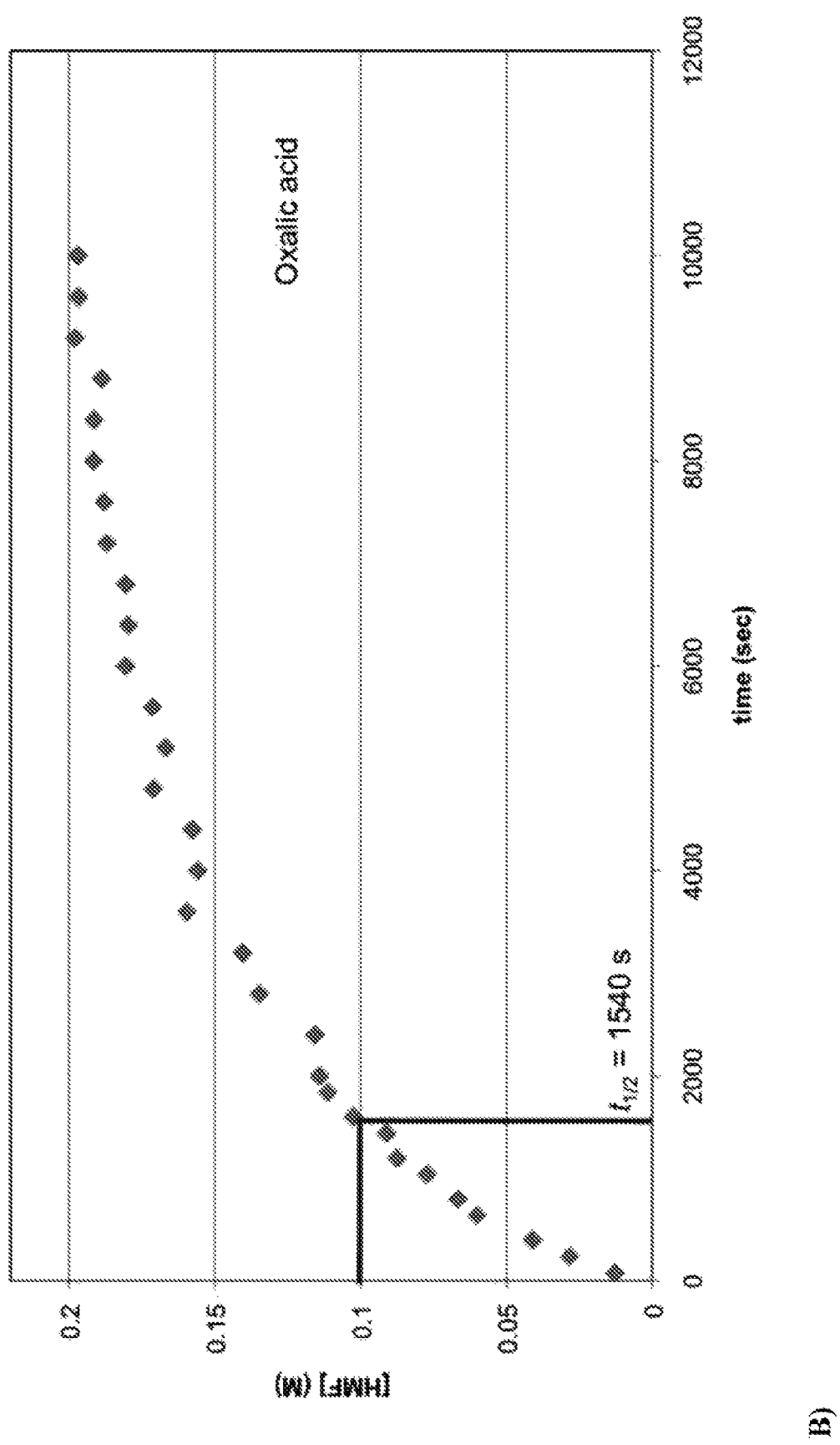
Figure 15:
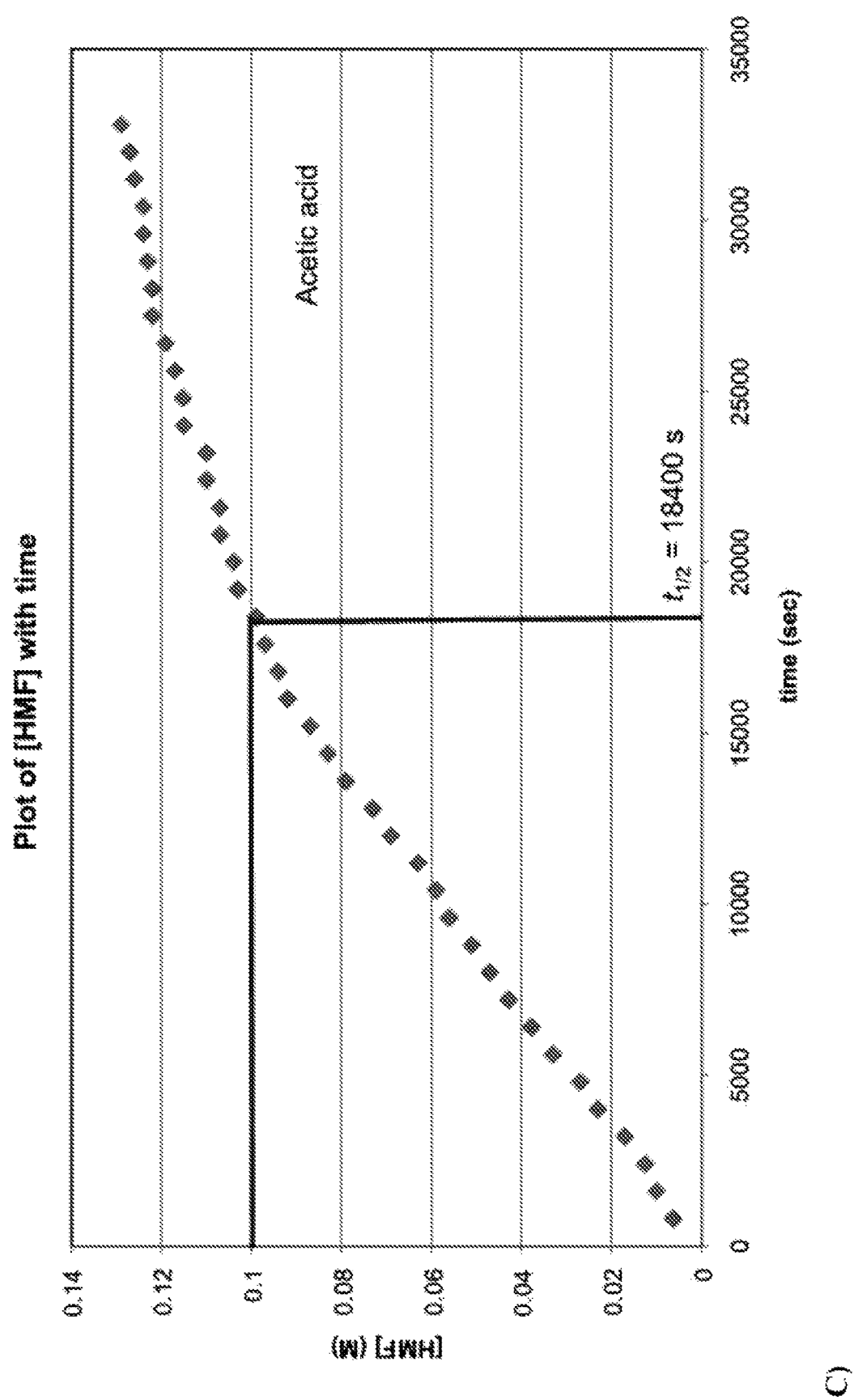

The concentration of HMF was plotted against time as shown in FIGS. 15A-C. Since 0.2 mmol of fructose starting material was used in each experiment, a theoretical maximum amount of 0.2 mmol of HMF was calculated as the product for each experiment. This assumes that the reaction goes to completion and that only one product, HMF, is formed. The time it took for 0.1 mmol of HMF, which is half the amount of the theoretical yield, to form was identified from the graphs in each experiment. Based on the above assumptions, the formation of 0.1 mmol of HMF corresponds to the consumption of 0.1 mmol of fructose. Thus, the amount of time to form 0.1 mmol of HMF relates to the time it takes for the consumption of half the amount of fructose in the reaction. This amount of time is referred in the summary chart below as "half-life" of the starting material.

| Entry | Acid | pK$_a$ | Half-life (sec) |
|---|---|---|---|
| 1 | Formic acid | 3.75 | 7340 |
| 2 | Oxalic acid | 1.27 | 1540 |
| 3 | Acetic acid | 4.76 | 18400 |

If more than one reaction product is formed or if the reaction does not proceed to completion, the "half-life" of fructose may vary.

Example 23

Preparation of 5-(hydroxymethyl)furfural (HMF) from Fructose and Amberlyst Catalyst This example demonstrates the conversion of fructose into HMF in DMSO using Amberlyst-15 as a solid catalyst. First, a solution of 20 g fructose in 5.6 mL of DMSO was prepared, and heated to a 90° C. The mixture was then cooled to ambient temperature before adding 60 mL tetrahydrofuran and 4.7 g of Amberlyst 15 were added. The mixture was reheated to 90° C. After 8 hrs, the orange-brown mixture was cooled to room temperature and gravity-filtered to collect the Amberlyst. The recovered catalyst was rinsed with THF. The filtrate was treated with 50 mL of water, and extracted with diethyl ether. After drying, ether extracts were evaporated under reduced pressure to obtain 10.48 g (75%) of HMF as a dark red-orange oil.

Example 24

Preparation of 5-(hydroxymethyl)furfural (HMF) and its Formate Ester from Fructose using Amberlyst Catalyst and Formic Acid This example demonstrates that the conversion of fructose to a mixture of HMF and FMF may be achieved by adding Amberlyst-15 to the formic acid solution. Moreover, this example demonstrates that adding a 3 Å molecular sieves further suppresses formation of levulinic acid in the dehydration step.

A mixture of 3.6 g of fructose, 0.43 g of Amberlyst-15, and 6.45 g 3 Å molecular sieves in 20 mL of formic was prepared and heated at 120° C. After 1 hour, the orange-brown mixture was cooled to room temperature, and analyzed by NMR spectroscopy. The product mixture contained fructose and HMF/FMF. No evidence for levulinic acid was observed in the product mixture.

The invention claimed is:

1. A method for preparing 2,5-dimethylfuran (DMF), 2,5-dimethyltetrahydrofuran, 2-methylfuran, or 2-methyltetrahydrofuran comprising the steps of:
   a) combining a compound of formula I with a carboxylic acid and a strong acid catalyst, wherein formula I has the structure:

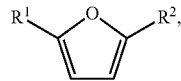

wherein one of $R^1$ and $R^2$ is selected from the group consisting of $CH_2OH$ and $CH(=O)$ and the other is selected from the group consisting of hydrogen, $CH_2OH$, $CH_3$, and $CH(=O)$;
   b) heating the reaction mixture of step (a) to a temperature sufficient to form an ester of formula I;
   c) adding an aprotic solvent and a first catalyst to the reaction mixture of step (b); and
   d) heating the reaction mixture of step (c) under hydrogen to foam a product selected from the group consisting of DMF, 2,5-dimethyltetrahydrofuran, 2-methylfuran, and 2-methyltetrahydrofuran.

2. The method according to claim 1, wherein the first catalyst of step (c) is a metal catalyst, wherein the metal catalyst is any one or more metal catalyst selected from the group consisting of palladium, iridium, platinum, ruthenium, nickel, rhodium, scandium, titanium, vanadium, chromium, manganese, iron, cobalt, copper, zinc, yttrium, zirconium, niobium, molybdenum, technetium, silver, cadmium, lanthanum, hafnium, tantalum, tungsten, rhenium, osmium, gold, and mercury.

3. The method according to claim 1, wherein the carboxylic acid is selected from the group consisting of formic acid, acetic acid, benzoic acid, trifluoroacetic acid, propionic acid, and trichloroacetic acid.

4. The method according to claim 3, wherein the carboxylic acid is selected from the group consisting of formic acid and acetic acid.

5. The method according to claim 1, wherein the strong acid catalyst is selected from the group consisting of sulfuric acid, hydrochloric acid, perchloric acid, hydrobromic acid, hydroiodic acid, p-toluenesulfonic acid, nitric acid, trifluoromethanesulfonic acid, methanesulfonic acid, and trifluoroacetic acid.

6. The method according to claim 5, wherein the strong acid catalyst is sulfuric acid.

7. The method according to claim 1, wherein the compound of formula I is selected from the group consisting of

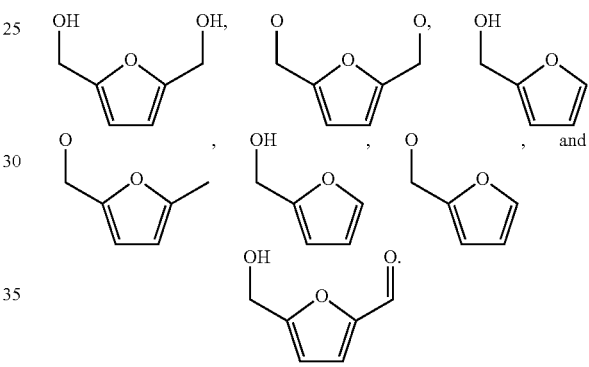

8. The method according to claim 5, wherein the compound of formula I is selected from the group consisting of

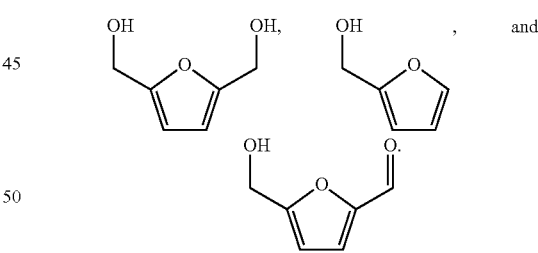

9. The method according to claim 1, wherein the compound of formula I is 5-(hydroxymethyl)furfural (HMF) or 2,5-bis(hydroxymethyl)furan (BHMF), and the product is DMF.

10. The method according to claim 1, wherein the compound of formula I is furfuryl alcohol and the product is 2-methylfuran.

11. The method according to claim 1, wherein the compound of formula I is HMF, and the product is 2,5-dimethyltetrahydrofuran.

12. The method according to claim 1, wherein the compound of formula I is furfuryl alcohol and the product is 2-methyltetrahydrofuran.

* * * * *